US010321832B2

(12) United States Patent
Berg et al.

(10) Patent No.: US 10,321,832 B2
(45) Date of Patent: Jun. 18, 2019

(54) SYSTEM AND METHOD FOR MONITORING BIOMETRIC SIGNALS

(71) Applicant: MAD Apparel, Inc., Redwood City, CA (US)

(72) Inventors: James Berg, San Francisco, CA (US); Hamid Butt, Cupertino, CA (US); Dhananja Jayalath, Redwood City, CA (US)

(73) Assignee: Mad Apparel, Inc., Redwood City, CA (US)

(*) Notice: Subject to any disclaimer, the term of this patent is extended or adjusted under 35 U.S.C. 154(b) by 846 days.

(21) Appl. No.: 14/702,129

(22) Filed: May 1, 2015

(65) Prior Publication Data
US 2015/0230719 A1 Aug. 20, 2015

Related U.S. Application Data

(63) Continuation-in-part of application No. 14/541,446, filed on Nov. 14, 2014.
(Continued)

(51) Int. Cl.
A61B 5/04 (2006.01)
A61B 5/00 (2006.01)
(Continued)

(52) U.S. Cl.
CPC .............. A61B 5/04 (2013.01); A61B 5/0024 (2013.01); A61B 5/0205 (2013.01);
(Continued)

(58) Field of Classification Search
CPC .... A61B 5/0408; A61B 5/6804; A61B 5/0024
(Continued)

(56) References Cited

U.S. PATENT DOCUMENTS 3,534,727 A 10/1970 Roman
3,973,099 A 8/1976 Morris
(Continued)

FOREIGN PATENT DOCUMENTS

KR 2014 0008971 A 1/2014
WO WO 01/15286 A1 3/2001
(Continued)

OTHER PUBLICATIONS

PCT International Search Report and Written Opinion, PCT Application No. PCT/US2015/028900, dated Jul. 30, 2015, 12 pages.
(Continued)

Primary Examiner — Carl H Layno
Assistant Examiner — Dacheng Xie
(74) Attorney, Agent, or Firm — Fenwick & West LLP

(57) ABSTRACT

A system for monitoring biometric signals of a user comprising: a garment configured to be worn by the user and comprising a mounting module having an array of connection regions; a set of biometric sensors coupled to the garment and configured to communicate with the array of connection regions to receive and transmit biometric signals indicative of muscle activity of the user; and a portable control module configured to couple to the garment in a first configuration and to decouple from the garment in a second configuration and comprising: a housing comprising an array of openings; a set of contacts, each including a first region that seals at least one of the array of openings and couples to at least one of the array of connection regions in the first configuration, and an electronics subsystem coupled to the housing and in communication with a second region of each contact.

18 Claims, 19 Drawing Sheets

Related U.S. Application Data

(60) Provisional application No. 62/078,078, filed on Nov. 11, 2014, provisional application No. 62/077,781, filed on Nov. 10, 2014, provisional application No. 62/016,373, filed on Jun. 24, 2014, provisional application No. 62/013,405, filed on Jun. 17, 2014, provisional application No. 61/908,077, filed on Nov. 23, 2013.

(51) Int. Cl.
    *B29C 45/00* (2006.01)
    *A61B 5/0205* (2006.01)
    *A61B 5/11* (2006.01)
    *B29L 31/34* (2006.01)
    *B29L 31/26* (2006.01)
    *B29K 75/00* (2006.01)
    *A61B 5/024* (2006.01)
    *A61B 5/053* (2006.01)
    *A61B 5/08* (2006.01)

(52) U.S. Cl.
    CPC .......... *A61B 5/1118* (2013.01); *A61B 5/6804* (2013.01); *B29C 45/0001* (2013.01); *A61B 5/0022* (2013.01); *A61B 5/024* (2013.01); *A61B 5/0533* (2013.01); *A61B 5/0816* (2013.01); *A61B 5/1112* (2013.01); *A61B 5/743* (2013.01); *A61B 2562/0214* (2013.01); *A61B 2562/04* (2013.01); *A61B 2562/12* (2013.01); *A61B 2562/125* (2013.01); *A61B 2562/14* (2013.01); *A61B 2562/164* (2013.01); *A61B 2562/166* (2013.01); *A61B 2562/182* (2013.01); *B29K 2075/00* (2013.01); *B29K 2855/02* (2013.01); *B29K 2995/0005* (2013.01); *B29L 2031/26* (2013.01); *B29L 2031/34* (2013.01); *Y10T 29/4913* (2015.01)

(58) Field of Classification Search
    USPC .................................................. 600/300–301
    See application file for complete search history.

(56) References Cited

U.S. PATENT DOCUMENTS

| | | | |
|---|---|---|---|
| 3,982,529 A | 9/1976 | Sato | |
| 4,400,341 A | 8/1983 | Sorensen | |
| 4,706,680 A | 11/1987 | Keusch et al. | |
| 4,729,377 A | 3/1988 | Granek et al. | |
| 4,799,441 A | 1/1989 | Boser | |
| 6,002,957 A | 12/1999 | Finneran | |
| 6,350,129 B1 | 2/2002 | Gorlick | |
| 6,381,482 B1 | 4/2002 | Jayaraman et al. | |
| 6,970,731 B1 | 11/2005 | Jayaraman et al. | |
| 6,978,684 B2 | 12/2005 | Nurse | |
| 7,173,437 B2 | 2/2007 | Hervieux et al. | |
| 7,474,910 B2 | 1/2009 | Hassonjee et al. | |
| 7,559,902 B2 | 7/2009 | Ting et al. | |
| 7,602,301 B1 | 10/2009 | Stirling et al. | |
| 7,783,334 B2 | 8/2010 | Nam et al. | |
| 7,821,407 B2 | 10/2010 | Shears et al. | |
| 7,825,815 B2 | 11/2010 | Shears et al. | |
| 7,978,081 B2 | 7/2011 | Shears et al. | |
| 8,006,633 B2 | 8/2011 | Bennett et al. | |
| 8,032,199 B2 | 10/2011 | Linti et al. | |
| 8,146,171 B2 | 4/2012 | Chung et al. | |
| 8,214,007 B2 | 7/2012 | Baker et al. | |
| 8,267,701 B2 | 9/2012 | Beaman et al. | |
| 8,280,503 B2 | 10/2012 | Linderman | |
| 8,475,371 B2 | 7/2013 | Derchak et al. | |
| 8,560,044 B2 | 10/2013 | Kurzweil et al. | |
| 8,750,959 B2 | 6/2014 | Lindberg et al. | |
| 8,798,708 B2 | 8/2014 | Tremblay | |
| 8,818,478 B2 | 8/2014 | Scheffler et al. | |
| 8,821,305 B2 | 9/2014 | Cusey et al. | |
| 8,909,318 B2 | 12/2014 | Nordstrom | |
| 2004/0187184 A1 | 9/2004 | Rubin et al. | |
| 2004/0254624 A1 | 12/2004 | Johnson | |
| 2005/0177059 A1 | 8/2005 | Koivumaa et al. | |
| 2005/0178201 A1 | 8/2005 | Impio et al. | |
| 2006/0264730 A1 | 11/2006 | Stivoric et al. | |
| 2007/0038057 A1 | 2/2007 | Nam et al. | |
| 2007/0285868 A1 | 12/2007 | Lindberg et al. | |
| 2008/0092341 A1 | 4/2008 | Ahmadshahi | |
| 2008/0096726 A1 | 4/2008 | Riley et al. | |
| 2008/0278899 A1 | 11/2008 | Hotelling et al. | |
| 2008/0288026 A1* | 11/2008 | Cross ................... A61B 5/0408 607/60 |
| 2009/0012408 A1 | 1/2009 | Nagata et al. | |
| 2009/0024017 A1 | 1/2009 | Ruffini et al. | |
| 2009/0270689 A1 | 10/2009 | Galland | |
| 2010/0037489 A1 | 2/2010 | Berner et al. | |
| 2010/0041974 A1 | 2/2010 | Ting et al. | |
| 2010/0117837 A1 | 5/2010 | Stirling et al. | |
| 2010/0185398 A1 | 7/2010 | Berns et al. | |
| 2010/0204616 A1 | 8/2010 | Shears et al. | |
| 2010/0234715 A1 | 9/2010 | Shin et al. | |
| 2010/0251454 A1 | 10/2010 | Kiernan | |
| 2010/0324405 A1 | 12/2010 | Niemi et al. | |
| 2011/0015498 A1 | 1/2011 | Mestrovic et al. | |
| 2011/0257546 A1 | 10/2011 | Gozzini et al. | |
| 2011/0288605 A1 | 11/2011 | Kaib et al. | |
| 2012/0068759 A1 | 3/2012 | Clark et al. | |
| 2012/0165645 A1 | 6/2012 | Russell et al. | |
| 2012/0208156 A1 | 8/2012 | Rocklin | |
| 2012/0330126 A1 | 12/2012 | Hoppe et al. | |
| 2013/0077263 A1 | 3/2013 | Oleson et al. | |
| 2013/0137943 A1 | 5/2013 | Rodrigues | |
| 2013/0137956 A1 | 5/2013 | Okuda et al. | |
| 2013/0172722 A1 | 7/2013 | Ninane et al. | |
| 2013/0192071 A1 | 8/2013 | Esposito et al. | |
| 2013/0198867 A1 | 8/2013 | Ricci et al. | |
| 2013/0245388 A1 | 9/2013 | Rafferty et al. | |
| 2013/0324368 A1 | 12/2013 | Aragones et al. | |
| 2014/0070949 A1 | 3/2014 | Chen | |
| 2014/0070957 A1 | 3/2014 | Longinotti-Buitoni et al. | |
| 2014/0097944 A1 | 4/2014 | Fastert et al. | |
| 2014/0135593 A1 | 5/2014 | Jayalth et al. | |
| 2014/0172134 A1 | 6/2014 | Meschter | |
| 2014/0180023 A1 | 6/2014 | Stivoric et al. | |
| 2014/0189928 A1 | 7/2014 | Oleson et al. | |
| 2014/0275888 A1 | 9/2014 | Wegerich et al. | |
| 2014/0278125 A1 | 9/2014 | Balakrishnan et al. | |
| 2014/0296651 A1 | 10/2014 | Stone | |
| 2014/0343391 A1 | 11/2014 | Korkala et al. | |
| 2014/0352023 A1 | 12/2014 | Mordecai et al. | |
| 2015/0047091 A1 | 2/2015 | Fournier et al. | |
| 2015/0148619 A1 | 5/2015 | Berg et al. | |
| 2015/0181692 A1 | 6/2015 | Jezewski et al. | |

FOREIGN PATENT DOCUMENTS

| | | |
|---|---|---|
| WO | 2006119345 A2 | 11/2006 |
| WO | WO 2007/063436 A1 | 6/2007 |

OTHER PUBLICATIONS

European Extended Search Report, European Application No. 15847342.1, dated Mar. 13, 2018, 8 pages.
European Extended Search Report, European Application No. 15809222.1, dated Mar. 29, 2018, 9 pages.
StudSeal press release, Douglas Electrical Components, http://news.thomasnet.com/fullstory/hermetic-feedthroughs-suit-highcurrent-applications-827050, May 21, 2009.
PCT International Search Report and Written Opinion, PCT Application No. PCT/US15/52969, dated Dec. 29, 2015, 11 pages.
United States Office Action, U.S. Appl. No. 14/541,446, dated Jun. 27, 2018, 28 pages.
United States Office Action, U.S. Appl. No. 14/541,446, dated Sep. 18, 2017, 20 pages.

(56) References Cited

OTHER PUBLICATIONS

United States Office Action, U.S. Appl. No. 14/541,446, dated Feb. 23, 2017, 13 pages.

* cited by examiner

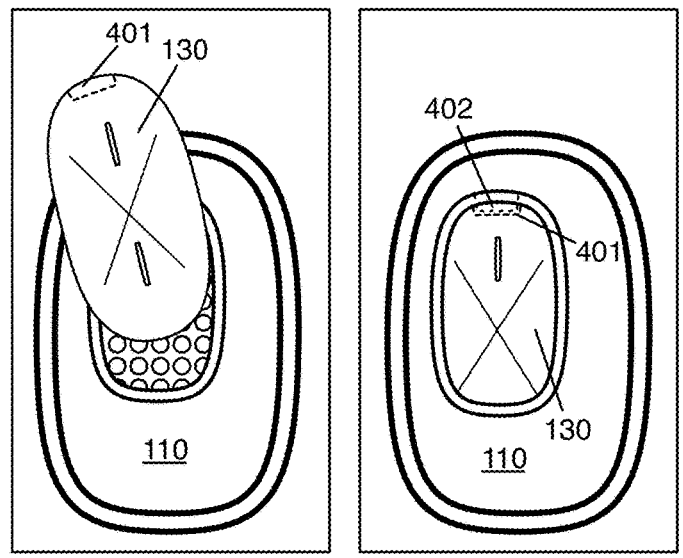
FIGURE 8C
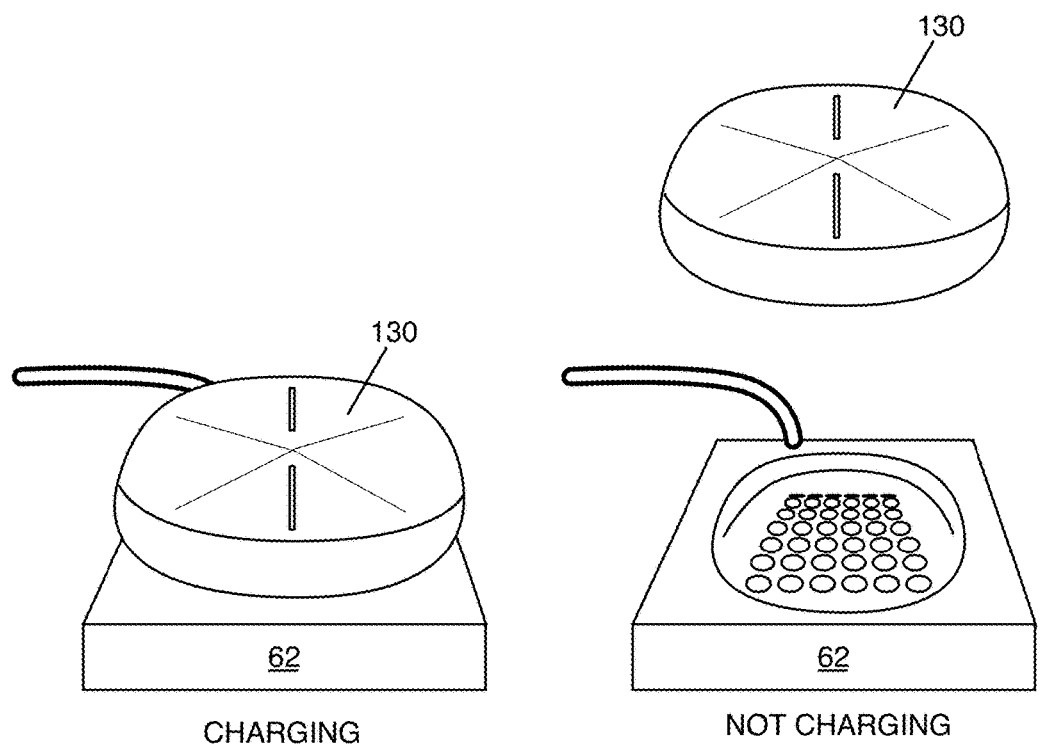
CHARGING  
FIGURE 9A
NOT CHARGING  
FIGURE 9B

EXAMPLE IMAGES FROM AN
EXERCISE-MONITORING APPLICATION
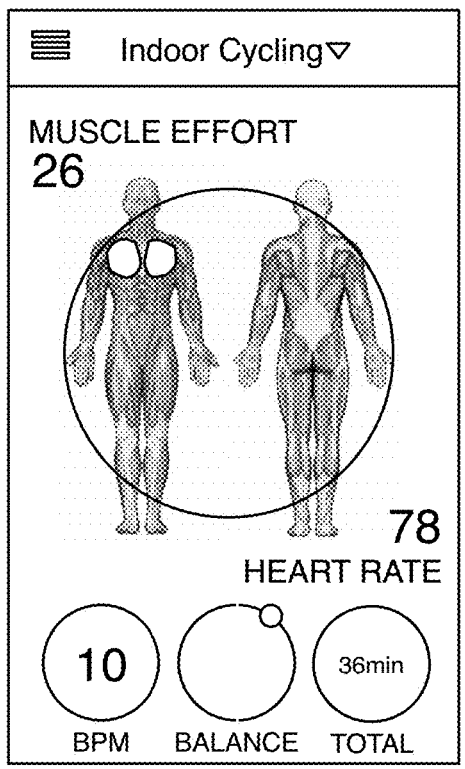
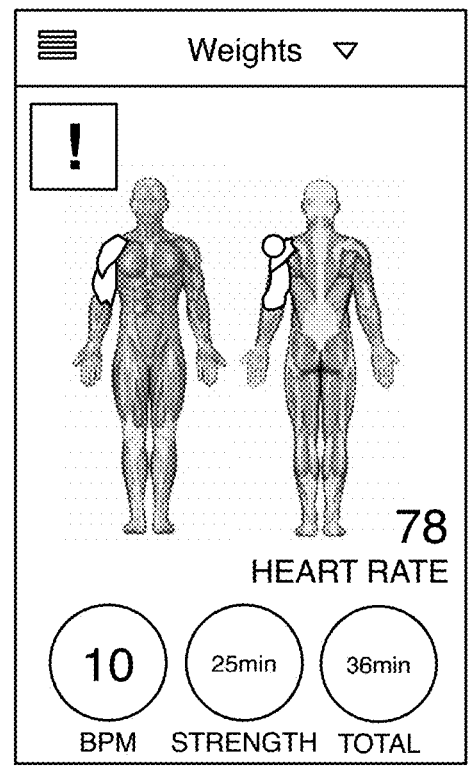
FIGURE 11A
FIGURE 11B

SYSTEM AND METHOD FOR MONITORING BIOMETRIC SIGNALS

CROSS-REFERENCE TO RELATED APPLICATIONS

This application is a continuation-in-part application of U.S. application Ser. No. 14/541,446 filed 14 Nov. 2014, which claims the benefit of U.S. Provisional Application Ser. No. 61/908,077 filed 23 Nov. 2013, U.S. Provisional Application Ser. No. 62/013,405 filed 17 Jun. 2014, U.S. Provisional Application Ser. No. 62/016,373 filed 24 Jun. 2014, and U.S. Provisional Application Ser. No. 62/077,781 filed 10 Nov. 2014, which are each incorporated in its entirety herein by this reference. This application also claims the benefit of U.S. Provisional Application Ser. No. 62/078,078 filed 11 Nov. 2014, which is also incorporated in its entirety herein by this reference.

TECHNICAL FIELD

This invention relates generally to the biometric device field, and more specifically to a new and useful system and method for monitoring biometric signals.

BACKGROUND

Tracking biometric parameters resulting from periods of physical activity can provide profound insights into improving one's performance and overall health. Historically, users have tracked their exercise behavior by manually maintaining records of aspects of their physical activity, including time points, durations, and/or other metrics (e.g., weight lifted, distance traveled, repetitions, sets, etc.) of their exercise behavior. Exercise tracking systems and software have been recently developed to provide some amount of assistance to a user interested in tracking his/her exercise behavior; however, such systems and methods still suffer from a number of drawbacks. In particular, many systems require a significant amount of effort from the user (e.g., systems rely upon user input prior to and/or after a period of physical activity), capture insufficient data (e.g., pedometers that estimate distance traveled, but provide little insight into an amount of physical exertion of the user), provide irrelevant information to a user, and are incapable of detecting body-responses to physical activity at a resolution sufficient to provide the user with a high degree of body awareness. Other limitations of conventional biometric monitoring devices include one or more of: involvement of single-use electrodes, involvement of a single electrode targeting a single body location, use of adhesives for electrode placement, contributions to user discomfort, and other deficiencies.

There is thus a need in the biometric device field to create a new and useful system and method for monitoring biometric signals. This invention provides such a new and useful system and method.

BRIEF DESCRIPTION OF THE FIGURES

FIG. 8C depicts a variation of a configuration between portions of a system for monitoring biometric signals of a user;

FIGS. 9A-9B depict configurations of charging modules in an example of a system for monitoring biometric signals of a user;

FIGS. 11A-11B depict examples of portions of an exercise-monitoring application in a method and/or system for monitoring biometric signals of a user;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1:
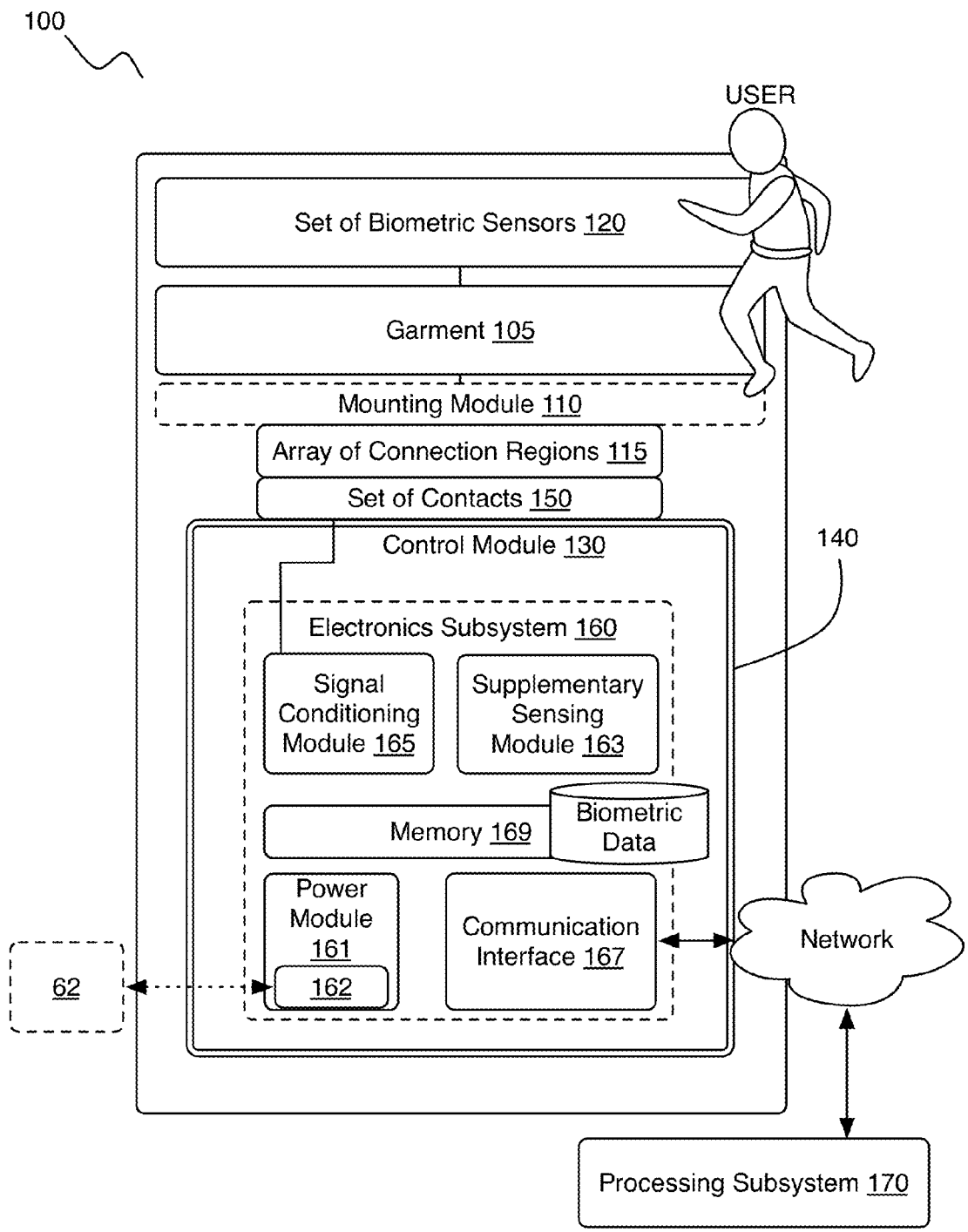
FIG. 1 depicts an embodiment of a system for monitoring biometric signals of a user.
Figure 2:
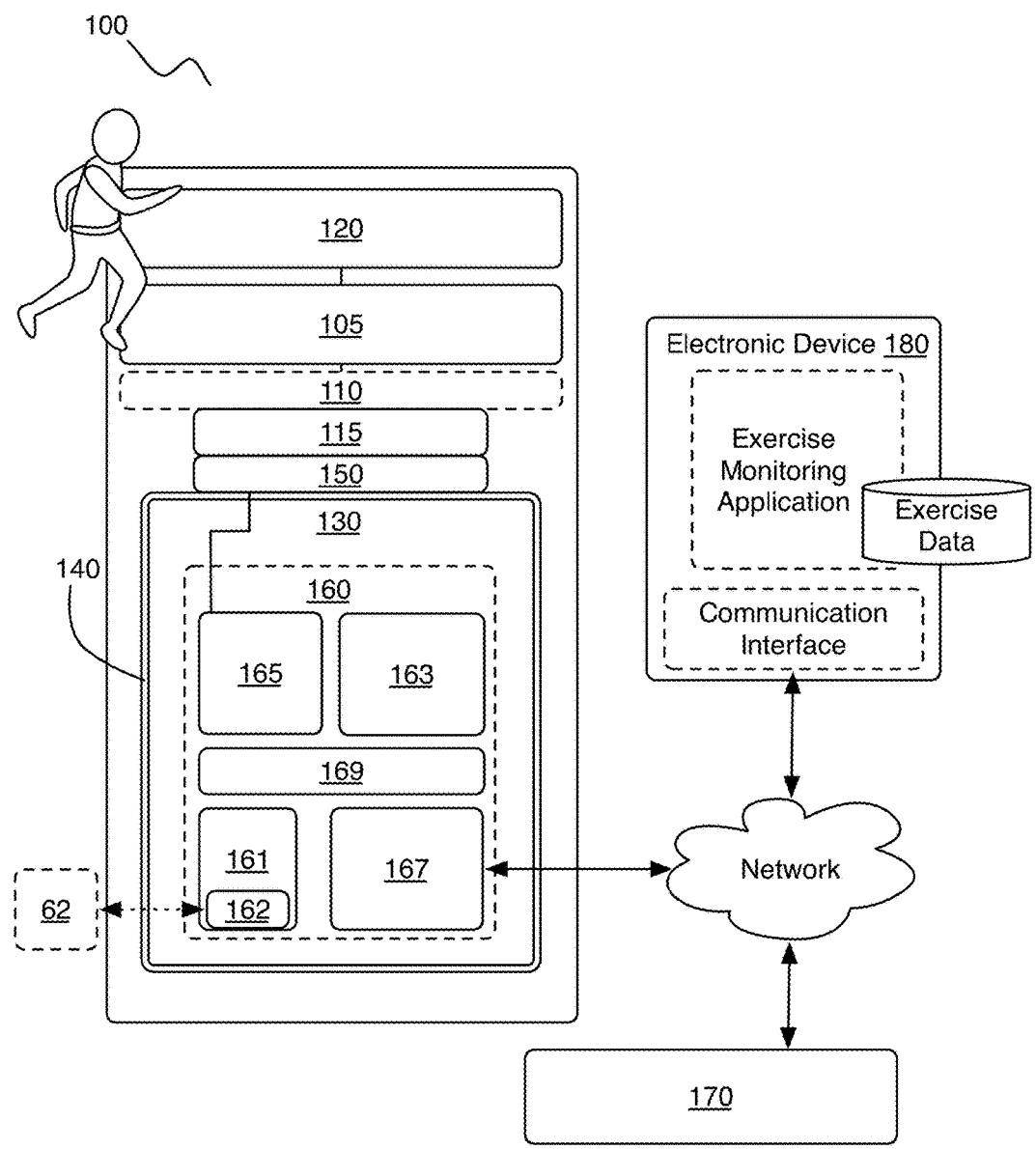
FIG. 2 depicts an embodiment of a system for monitoring biometric signals of a user, in communication with an external electronic device.

As shown in FIGS. 1 and 2, an embodiment of a system 100 for monitoring biometric signals of a user comprises: a garment 105; a set of biometric sensors 120 coupled to the garment and configured to receive biometric signals indicative of muscle activity of the user; and a control module 130 comprising a housing 140, a set of contacts 150 configured to couple to an array of connection regions 115 that enable signal transmission from the set of biometric sensors, and an electronics subsystem 160 in communication with the set of contacts. In some embodiments, the system 100 can further comprise one or more of: a mounting module 110 coupled to the garment and providing the array of connection regions; and a processing subsystem 170 configured to communicate with the electronics subsystem 160 and generate analyses based upon biometric signals detected by way of the set of biometric sensors.

The system 100 functions to position a set of biometric sensors at desired regions of a user's body, in order to detect biometric signals generated during physical activity of the user. The system 100 also functions to process detected biometric signals and to provide information derived from the processed biometric signals to the user performing a physical activity in substantially near real time, such that the user can gain insights into how to maintain or improve performance of the physical activity in a beneficial manner. In variations, the system 100 is configured to detect and process bioelectrical signals generated at a set of regions of the body of a user who is exercising (e.g., performing aerobic exercise, performing anaerobic exercise), and to present analyses in a visual manner (e.g., graphic manner, textual manner) by way of an application executing at an electronic device having a display. As such, bioelectrical signals detectable, processable, and/or analyzable by the system 100 can include any one or more of: electromyograph (EMG) signals, electrocardiography (ECG) signals, electroencephalograph (EEG) signals, magnetoencephalograph (MEG) signals, galvanic skin response (GSR) signals, electrooculograph (EOG) signals, and any other suitable bioelectrical signal of the user. The system 100 can, however, be configured to detect, process, and/or analyze any other suitable biosignal data of the user, including one or more of: heart rate data, movement data, respiration data, location data, environmental data (e.g., temperature data, light data, etc.), and any other suitable data.

In one embodiment, the system 100 can be configured to aggregate a combination of one or more of the biometric factors described above, and to determine and output a variety of metrics associated with the user's exercise activity. These metrics can provide the user with insights pertaining to his/her muscle exertion, muscle balance, exercise form, potential to incur injuries (e.g., acute injuries, chronic injuries), muscle fatigue, activity levels, muscle recovery behavior, exercise regimen parameters (e.g., types of exercise, sets of an exercise, repetitions of an exercise, etc.), and/or any other suitable exercise- or health-related factor.

The system 100 is preferably configured to be used by a user who is away from a research or clinical setting, such that the user is interfacing with a portion of the system 100 while he or she undergoes periods of activity in a natural setting (e.g., at a gym, outdoors, etc.). The system 100 can additionally or alternatively be configured to be operated by a user who is in a research setting, a clinical setting, or any other suitable setting. The system 100 is preferably configured to perform at least a portion of the method 200 described in Section 2 below; however, the system 100 can additionally or alternatively be configured to perform any other suitable method.

1.1 System—Garment and Sensors

The garment 105 functions to position a set of biometric sensors proximal a set of body regions of the user, in order to enable detection of biometric signals from specific body regions of the user as the user is performing a form of physical exercise. The garment 105 can thus provide a means for providing close coupling and/or consistent placement of the set of biometric sensors at the body of the user. As such, the garment can be a form-fitting garment that provides a biasing force on the set of biometric sensors 120 described below, in order to promote close coupling between the set of biometric sensors 120 and desired portions of the body of the user. The garment can thus include a stretchable and/or compressive fabric comprising natural and/or synthetic fibers (e.g., nylon, lycra, polyester, spandex, etc.) to promote coupling (i.e., electrical coupling, mechanical coupling) and/or reduce motion artifacts that could otherwise result from relative motion between the skin of the user and the sensors of the set of biometric sensors 120. In examples, the garment 105 can include any one or more of: a top (e.g., shirt, jacket, tank top, etc.), bottom (e.g., shorts, pants, etc.), elbow pad, knee pad, arm sleeve, leg sleeve, socks, undergarment, neck wrap, glove, and any other suitable wearable garment. In some embodiments, the system 100 can comprise an embodiment of the garment described in U.S. application Ser. No. 14/079,629 entitled "Wearable Architecture and Methods for Performance Monitoring, Analysis, and Feedback" and filed on 13 Nov. 2013, which is herein incorporated in its entirety by this reference. However, the system 100 can alternatively comprise any other suitable garment.

Figure 3A:
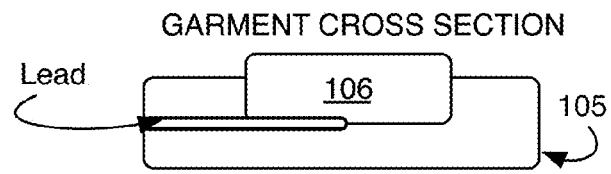
FIG. 3A depicts a cross-section of a portion of an embodiment of a system for monitoring biometric signals of a user.

In providing close coupling between the set of biometric sensors, as described below, and the body of the user, the garment 105 preferably comprises a plurality of conductive regions 106, as shown in FIG. 3A, configured to contact the set of body regions of the user from which biometric signal detection is desired, when the garment is worn by the user. As such, the plurality of conductive regions 106 can facilitate biometric signal transduction to the set of biometric sensors 120 described below. Preferably, the plurality of conductive regions 106 includes volumes of a conductive material that is integrated into the garment, wherein the conductive material is flexible, has good fatigue resistance, and is biocompatible (e.g., does not induce an allergic response, does not promote harboring of bacteria, etc.). The plurality of conductive regions 106 preferably also provide direct interfaces with the skin of the user when the garment is worn by the user, in order to facilitate electrical coupling with low impedance. However, in alternative variations, the plurality of conductive regions 106 can alternatively not directly contact skin of the user, but be configured to electrically couple to the user by way of an electrical coupling medium (e.g., saline, sweat, electrolyte medium, etc.) transmitted by way of the garment 105 or the user. In variations, the plurality of conductive regions 106 can include a conductive resin or silicone material formed directly onto a surface of the garment 105 facing the skin of the user, when the garment 105 is worn by the user, in order to facilitate signal transduction from the user to the set of biometric sensors 120 of the system 100. However, the conductive material can alternatively comprise any other suitable material and/or be configured in any other suitable manner.

The set of biometric sensors 120 is preferably coupled to the garment and configured to receive biometric signals indicative of muscle activity of the user. As such, the set of biometric sensors 120 function to detect bioelectric potentials (i.e., biopotentials) from body regions of the user, which vary according to different states of activity of the user. The set of biometric sensors 120, as described above, are preferably incorporated with or otherwise coupled to the plurality of conductive regions 106 of the garment 105; however, the set of biometric sensors 120 can include one or more biometric sensors that are configured to couple to the user in any other suitable manner (e.g., without involvement of the garment 105, without involvement of a plurality of conductive regions 106 of the garment 105).

The set of biometric sensors 120 preferably include electromyography (EMG) electrodes configured to acquire biopotential signals resulting from muscle activity of the user. However, in some variations, the set of biometric sensors 120 can additionally or alternatively include any one or more of: respiration sensors (e.g., sensors that operate according to plethysmography), galvanic skin response (GSR) sensors, temperature sensors, accelerometers (e.g., single axis accelerometers, multi-axis accelerometers), gyroscopes (e.g., single axis gyroscopes, multi-axis gyroscopes) global positioning system (GPS) sensors, vibration sensors, bioimpedance sensors, bend-angle measurement sensors, electrocardiography (ECG) sensors, sensors indicative of other cardiovascular parameters (e.g., pulse oximetry sensors, blood pressure sensors), and any other suitable type of sensor. As such, the set of biometric sensors 120 can detect biosignals indicative of one or multiple types of biological/physiological responses to activity of a user, in providing information relevant to exercise behavior of the user.

Figure 3B:
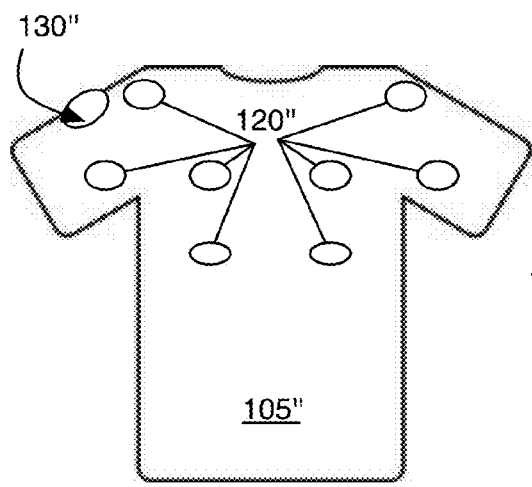
FIGS. 3B-3C depict different variations of garments in an embodiment of a system for monitoring biometric signals of a user.

Preferably, the type, number, and positioning of the set of biometric sensors is dependent upon the type(s) of garment(s) 105 included in the system 100. Additionally, for anatomical regions having contralateral pairs, the set of biometric sensors 120 preferably includes pairs of sensors, each pair including a first sensor at a first body region and a second sensor at a second body region that is a contralateral region to the first body region. In one variation, as shown in FIG. 3B, for a garment 105 that has a form factor of a top (e.g., shirt, tank top, etc.), the set of biometric sensors 120 can include a set of EMG electrodes configured to be positioned at desired locations when the garment 105 is worn by the user, and can additionally or alternatively include one or more of a heart rate sensor and a respiratory sensor. In one example of this variation, the set of EMG electrodes include electrodes configured to be positioned proximal one or more of: the pectoralisis muscles, the abdominal muscles, the oblique muscles, the trapezius muscles, the rhomboid muscles, the teres major muscles, the latissimus dorsi muscles, the deltoid muscles, the biceps muscles, and the triceps muscles when the garment 105 is worn by the user. In the example, the set of biometric sensors can further include a heart rate sensor configured to be positioned proximal the heart region of the user, and/or a respiratory sensor configured to encircle at least a portion of the torso of the user (i.e., to facilitate plethysmography) when the garment 105 is worn by the user. Variations of the example of the garment 105 configured as a top with biometric sensors can, however, be configured in any other suitable manner (e.g., a tank top garment can omit sensors positioned proximal the triceps and the biceps muscles).

Figure 3C:
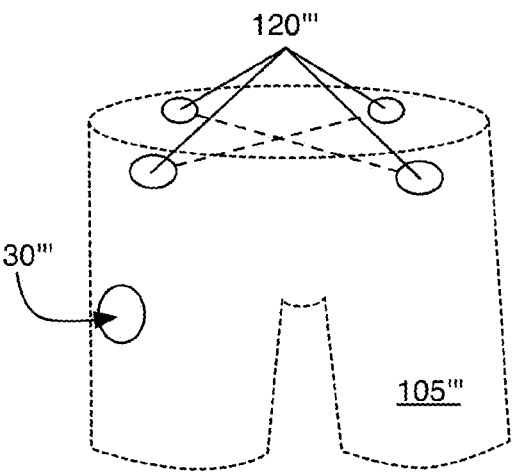
Figure 3D:
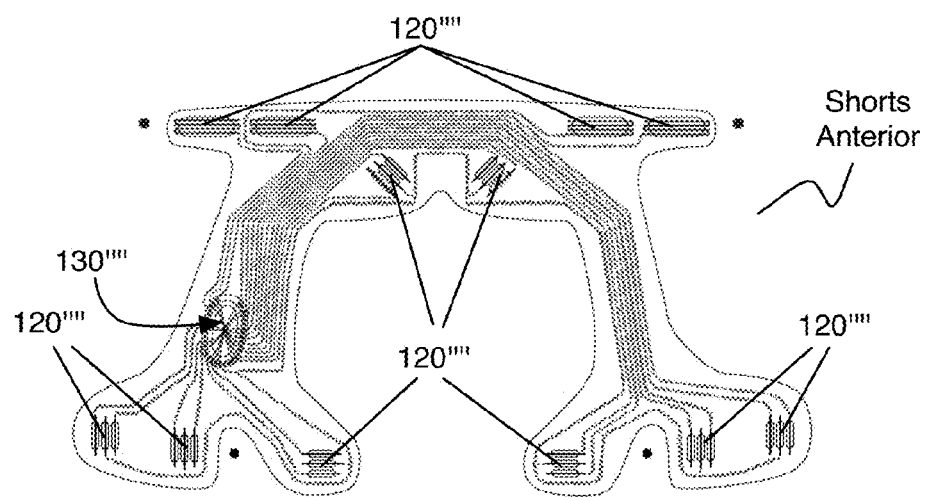
FIG. 3D depicts a specific example of a biometric sensor configuration in an embodiment of a system for monitoring biometric signals of a user.

In another variation, as shown in FIGS. 3C and 3D, for a garment 105 that has a form factor of a bottom (e.g., shorts, pants, etc.), the set of biometric sensors 120 can include a set of EMG electrodes configured to be positioned at desired locations when the garment 105 is worn by the user. In one example of this variation, the set of EMG electrodes include electrodes configured to be positioned proximal one or more of: the gluteus maximus muscles, the gluteus medius muscles, the vastus lateralis muscles, the gracilis muscles, the semimembranosus muscles, the semitendinosis muscles, the biceps femoris, the quadriceps muscles, the soleus muscles, the gastrocnemius muscles, the rectus femoris muscles, the sartorius muscles, the peroneus longus muscles, and the adductor longus muscles when the garment 105 is worn by the user. Variations of the example of the garment 105 configured as a bottom with biometric sensors can, however, be configured in any other suitable manner.

In alternative embodiments, the set of biometric sensors 120 can be supplemented with a set of supplementary sensors 125 configured to detect one or more aspects associated with an environment of the user. In variations, the set of supplementary sensors 125 can include one or more of: environmental temperature sensors, altimeters, oxygen content sensors, air quality sensors, near field communication (NFC) sensors (e.g., configured to detect a nearby device or piece of exercise equipment having a corresponding NFC element), and any other suitable supplementary sensor that can enrich the data acquired from user and/or the environment of the user.

1.2 System—Control Module

The control module 130 comprises a housing 140 and a set of contacts 150 configured to couple to an array of connection regions 115 in electrical communication with the set of biometric sensors 120, which enable signal transmission from the set of biometric sensors to the control module 130. The control module 130 preferably also includes an electronics subsystem 160 in communication with the set of contacts 150, wherein the electronics subsystem 160 facilitates signal reception, signal conditioning, signal transmission, and power distribution for the system 100. The control module 130 thus functions to control signal reception, preprocessing, and transmission to a processing subsystem, and to physically protect/isolate sensitive elements (e.g., electronics) of the system 100. The control module 130 is preferably configured to be a portable control module that can removably couple to the garment 105 and set of biometric sensors 120 in cooperation with a mounting module 110 of the garment 105, as described below. As such, the control module 130 can be configured to be uncoupled from the garment by the user (or another entity) when desired (e.g., during charging, during washing of the garment, during battery replacement, etc.). However, the control module 130 can alternatively be configured to semipermanently couple to the garment 105, such that it is not desirable for the user to remove the control module 130 from the garment. Furthermore, the control module 130 is preferably configured to provide electrical signal conduction pathways, through conductive contacts, in a waterproof manner; however, the control module 130 can alternatively be configured to provide electrical signal conduction pathways in any other suitable manner.

1.2.1 Control Module—Housing Assembly Configuration and Manufacture

The housing 140 functions to house and protect the electronics subsystem 160 over the lifetime of use of the system 100 by a user, and can further function to enhance wearability of the system. The housing 140 is preferably composed of a rigid material (e.g., a rigid plastic material, a metal, etc.), such that the housing 140 does not deform in response to normal forces, shear stresses, bending stresses, or torsional stresses induced during use of the system 100. Alternatively, the housing 140 can be flexible to facilitate maintenance of compliance with a user as the user performs a physical activity. In variations wherein the housing 140 is flexible, other elements of the system 100 can also be flexible (e.g., the electronics subsystem can comprise a flexible thin film battery, the electronics subsystem can comprise flexible electronics, etc.) to facilitate compliance with the body of a user. The housing 140 is preferably composed of a non-conductive material (i.e., in order to prevent bridging across elements that provide signal conduction); however, the housing 140 can alternatively be composed of any other suitable material and configured to prevent bridging in any suitable manner. In a specific example, the housing is composed of a polycarbonate/acyrlonitrile butadiene styrene (ABS) blend; however, variations of the specific example can alternatively be composed of only polycarbonate, only ABS, or any other suitable material.

Figure 4A:
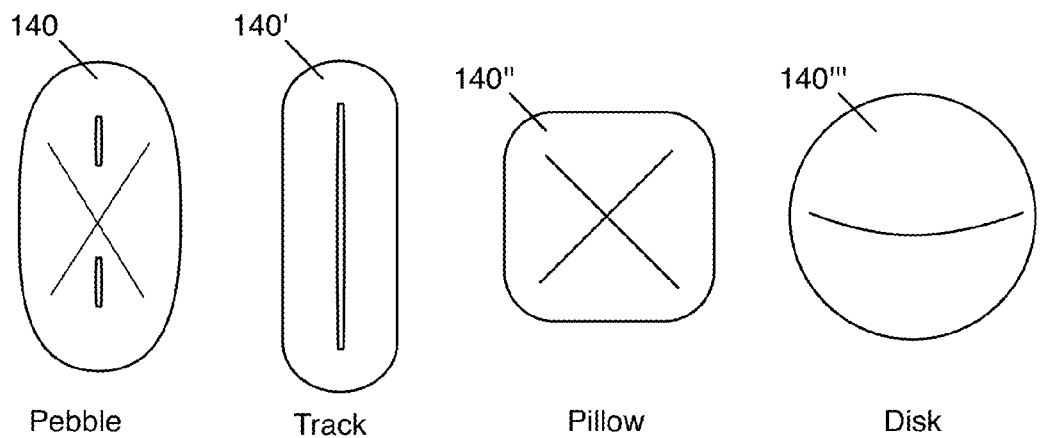
FIG. 4A depicts variations of a housing of a control module in an embodiment of a system for monitoring biometric signals of a user.
Figure 4B:
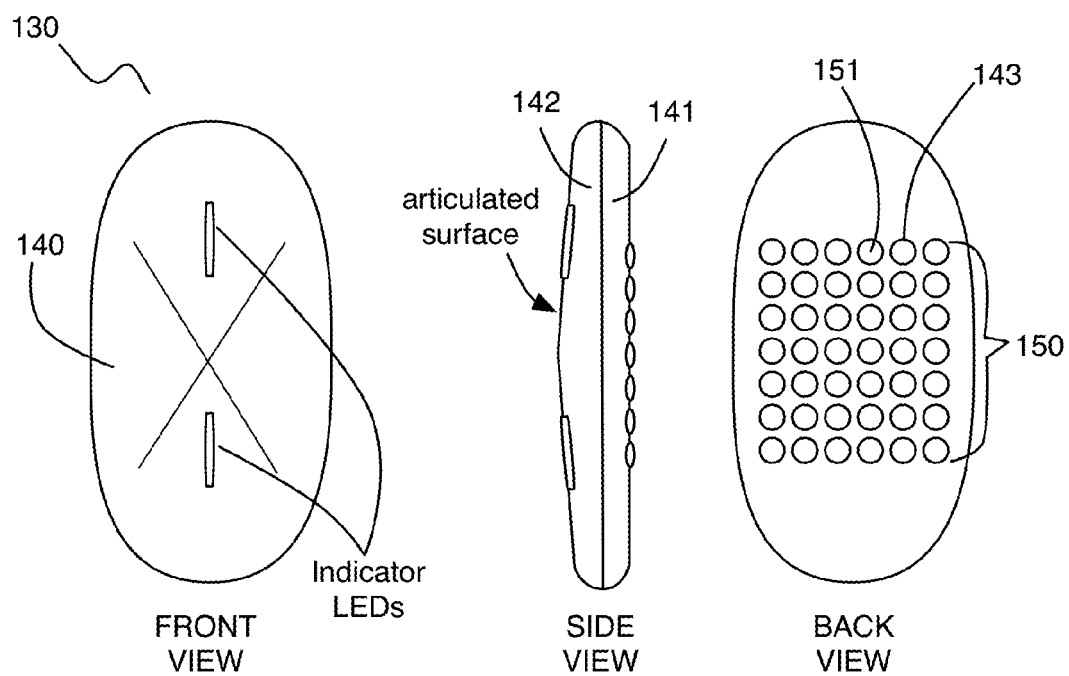
FIG. 4B depicts an example of a control module in an embodiment of a system for monitoring biometric signals of a user.

The housing 140 preferably has a profile that does not protrude a significant distance from the body of the user when the garment 105 is worn by the user. As such, the housing 140 preferably has a low aspect ratio that contributes to a thin form factor of the control module 130. However, the housing 140 can alternatively define a volume with a high aspect ratio. Preferably, the external surface of the housing 140 is substantially smooth and has rounded edges, in order to avoid damaging the garment 105 during motion of the user. Furthermore, the housing 140 can define a substantially polygonal footprint (i.e., triangular footprint with rounded edges, a quadrilateral footprint with rounded edges, a pentagonal footprint with rounded edges, a hexagonal footprint with rounded edges, etc.), or can alternatively define one or more of a circular footprint, an ellipsoidal footprint, and an amorphous footprint. In one example, as shown in FIG. 4B, the housing 140 defines an ellipsoidal footprint and has a thickness substantially below 2 cm, a height below 10 cm, and a width below 6 cm, in order to produce a smooth form factor with a low aspect ratio. In a specific example, as shown in FIG. 4B, the housing 140' has an ellipsoidal footprint with an overall thickness of ii mm, a shell thickness of 1.4 mm, a width of 34 mm, and a height of 62 mm. Variations of the example of the housing can, however, be configured in any other suitable manner, as shown in FIG. 4A.

The housing 140 preferably forms a shell about internal components of the control module 130, and preferably has a first housing portion 141 facing the body of the user when the control module 130 interfaces with the user and a second housing portion 142 facing away from the body of the user when the control module 130 interfaces with the user, an example of which is shown in FIG. 4B. The first housing portion 141 and/or the second housing portion 142 can comprise a concave surface or a convex surface, in interfacing with the garment or the body of the user. Furthermore, depending upon the intended position of the control module 130 relative to the garment 105 and/or the body of the user, the first housing portion 141 and/or the second housing portion 142 can define surfaces that are configured to conform to the body of the user upon coupling of the system 100 to the user. The first housing portion 141 and the second housing portion 142 can be coupled together using a sealing element (e.g., water tight sealing element), including one or more of: an adhesive, a compliant sealing material (e.g., putty), an o-ring, an x-ring, any other suitable ring, and/or any other suitable sealing element. Additionally or alternatively, portions of the housing 140 can be coupled in any other suitable manner (e.g., by ultrasonic welding, by use of a solvent, by a thermal bonding method, etc.) As such, an interface between the first housing portion 141 and the second housing portion 142 can be configured to be waterproof and/or machine-washable in order to protect aspects of the control module 130. In the specific example shown in FIG. 4B, the first housing portion 141 has an articulated surface configured to promote tactility, and ports that allow light transmission (e.g., from indicator LEDs) to inform the user regarding one or more statuses of the system 100 (e.g., proper coupling relative to other elements of the system 100, an active configuration of the control module 130, an inactive configuration of the control module 130, a charging status of the system 100, a calibration status of the system 100, etc.).

The housing 140 preferably has an array of openings 143 defined at one or more of the first housing portion 141 and the second housing portion 142, wherein the array of openings 143 provides access for a set of contacts 150 configured between the electronics subsystem 160 and an array of connection regions 115, as described in further detail below. Preferably, the array of openings 143 is defined entirely at the first housing portion 141; however, in alternative variations, the array of openings 143 can be defined at both the first housing portion 141 and the second housing portion 142, or at only the second housing portion 142. The array of openings 143 can comprise a rectangular array of openings (i.e., with openings of the array of openings 143 arranged in a rectangular grid pattern); however, the array of openings 143 can alternatively be configured in any other suitable manner (e.g., as a circular array of openings, as an ellipsoidal array of openings, as a polygonal array of openings, as an amorphous array of openings, etc.). Each opening in the array of openings 143 can be a circular opening or can alternatively be a non-circular opening. Furthermore, each opening in the array of openings 143 is preferably identical to every other opening in the array of openings 143 in morphology; however, the array of openings 143 can alternatively comprise non-identical openings. In a specific example, as shown in FIG. 4B the array of openings 143 includes 42 identical circular openings arranged in a 7×6 rectangular array, each opening having a diameter of 3 mm and an inter-opening spacing of 1.5 mm; however, variations of the specific example of the array of openings 143 can be configured in any other suitable manner.

The set of contacts 150 functions to facilitate coupling between the electronics subsystem 160 of the control module 130 and an array of connection regions 115, by way of the array of openings 143 of the housing 140 described above. In more detail, and in some variations, each contact in the set of contacts 150 can function to conduct an electrical signal to at least one electrical contact pad 53 of an electronics connection substrate 50 for signal transmission to the electronics subsystem 160, as described in further detail below. As such, the set of contacts 150 comprise electrically conductive contacts that facilitate reception of biosignals from the set of biometric sensors 120 of the system 100. In variations, the set of contacts 150 can provide conduction of biopotential signals and/or any other suitable electrical signals at a high input impedance and with low current requirements; however, the set of contacts 150 can alternatively be configured to conduct any other suitable types of signals under any other suitable constraints. Preferably, the set of contacts 150 comprises contacts composed of an electrically conductive, elastic, and compliant material (e.g., electrically conductive silicone, electrically conductive polymer, etc.) that facilitates maintenance of electrical communication between the set of biometric sensors 120 and the electronics subsystem 160 during motion of the user. In one example, the conductive polymer used in the set of contacts comprises an ether-based conductive thermoplastic polyurethane material; However, the set of contacts 150 can alternatively comprise one or more contacts composed of an electrically conductive, but non-elastic or non-compliant material (e.g., a metallic material).

Figure 5A:
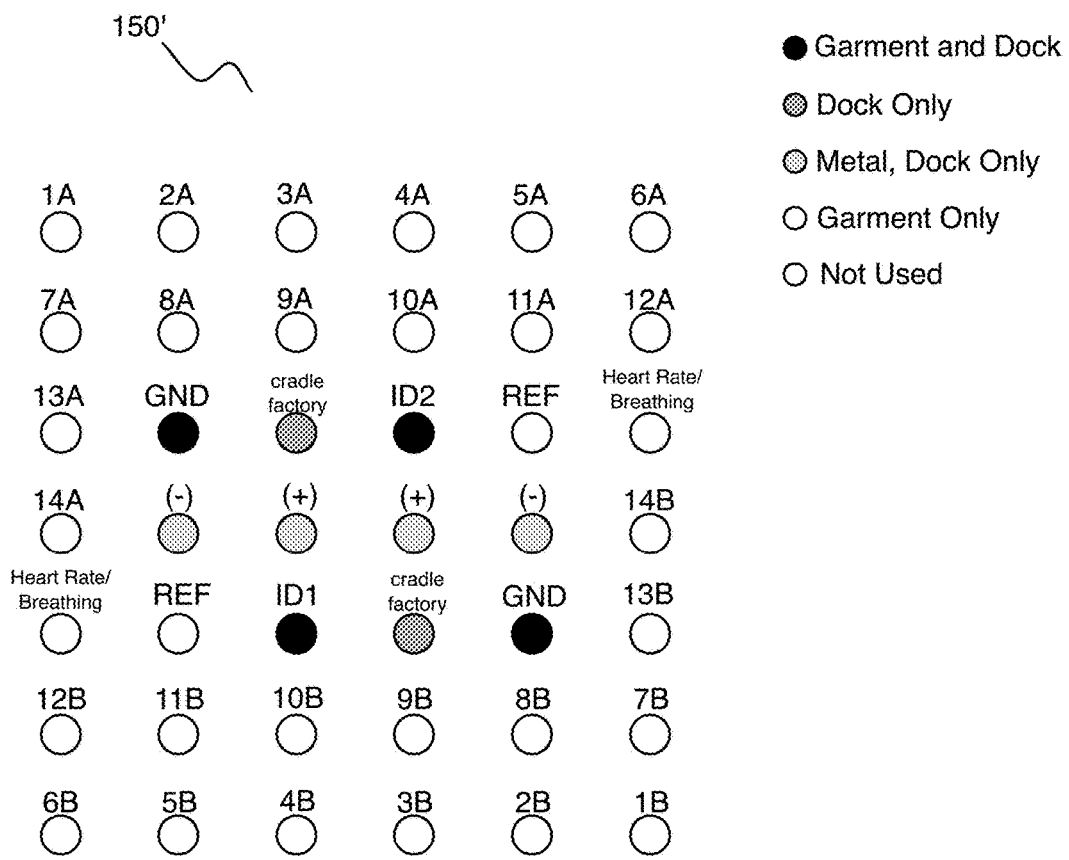
FIG. 5A depicts a first example configuration of contacts in an embodiment of a system for monitoring biometric signals of a user.
Figure 5B:
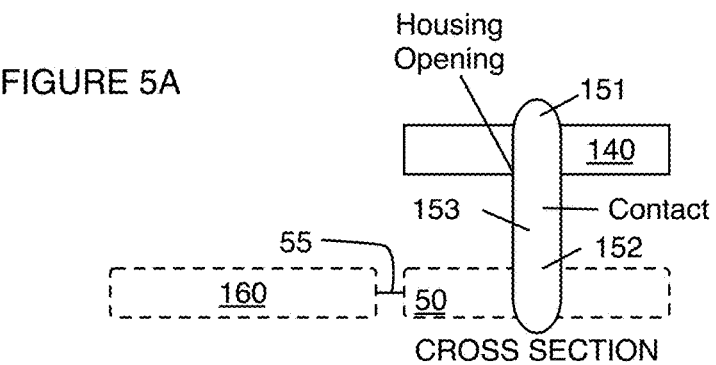
FIG. 5B depicts a cross-section of a portion of an embodiment of a system for monitoring biometric signals of a user.

As shown in FIG. 5B, each contact in the set of contacts 150 preferably includes a first region 151 that extends through at least one opening of the array of openings 143 of the housing 140, and a second region 152 that couples to a portion of an electronics connection substrate 50 and/or the electronics subsystem 160. The first region 151 of each contact in the set of contacts 150 preferably seals at least one opening in the array of openings 143 of the housing 140, in order to prevent fluids (e.g., water, sweat) from seeping into the housing and potentially damaging the electronics subsystem 160, which is otherwise accessible through the array of openings 143. As such, the housing 140 of the control module 130 is preferably configured to be waterproof and/or machine-washable, due to the configuration of the set of contacts 150 in relation to the housing 140. The first region 151 of each of the set of contacts 150 can thus be over-molded on the housing 140 at least at one opening of the array of openings 143, and the second region 152 can be over-molded onto or otherwise coupled to a desired region of the electronics subsystem 160, which is internal to the housing 140 of the control module 130. In more detail, as described further below and shown in FIGS. 13A-13F, the second region 152 of a contact can be coupled to an electrical contact pad 53 of a set of electrical contact pads 52 of an electronics connection substrate 50 in communication with the electronics subsystem 160. Finally, an intermediate region 153 of each contact can be configured to pass into an opening of the array of openings, such that the intermediate region 153 of the contact is surrounded by the first region 151 and the second region 152.

Each contact in the set of contacts 150 is preferably associated with an opening of the array of openings 150 in a one-to-one manner; however, the set of contacts 150 and the array of openings 143 can alternatively be configured in a less-than-one-to-one or a more-than-one-to-one manner. Furthermore, each contact in the set of contacts 150 is preferably isolated from other contacts (e.g., adjacent contacts), such that bridging of contacts does not occur. As such, the housing 140 and/or other portions of the system 100 can be configured to prevent bridging (e.g., due to an unintended fluid connection provided across contacts, due to any other unintended electrical connection provided across contacts). As such, regions of the control module 130 that are intermediate to contacts of the set of contacts 150 can include one or more of: shielding elements (e.g., electrical insulators) that prevent cross-contact bridging, wicking elements (e.g., conduits, absorbent regions) configured to control fluid positions and/or movement relative to contacts of the set of contacts 150, and any other suitable element(s) that prevent cross-contact bridging.

As shown in FIGS. 5B and 13A-13F, in relation to the set of contacts 150, the control module 130 can include an electronics connection substrate 50 that functions to conduct signals from the set of contacts 150 to the electronics subsystem 160. In particular, the electronics connection substrate 50 can be configured to couple to the first housing portion 141 by way of the set of contacts 150, and/or to be aligned with the first housing portion 141 during manufacturing of the control module 130 and coupling of the set of contacts to the electronics connection substrate 50. The electronics connection substrate 50 preferably includes a set of electrical contact pads 52 that align with the array of openings 143 of the first housing portion 141, as well as a linking interface 55 that couples each of the set of electrical contact pads 52 to the electronics subsystem 160 for signal processing and transmission. As such, the electronics connection substrate 50 can allow routing of signals from originating at first regions of the set of contacts 150 (i.e., at an exterior surface of the housing 140) to the electronics subsystem 160, by way of the linking interface 55.

The electronics connection substrate 50 is preferably flexible in order to facilitate manufacturing and assembly of the control module 130, for instance, in relation to alignment of the electronics connection substrate 50 relative to the housing 140, and/or coupling of the set of contacts 150 to both the housing 140 and the electronics connection substrate 50. Furthermore, the electronics connection substrate 50 preferably includes signal routing pathways (e.g., conductive leads) coupled to the set of electrical contact pads 52 and to the linking interface 55, thereby enabling signal routing to the electronics subsystem 160. However, at least a portion of the electronics connection substrate 50 can alternatively be composed of a rigid material, and/or the electronics connection substrate 50 can facilitate signal routing from the set of electrical contact pads 52 to the electronics subsystem 160 in any other suitable manner. In a specific example, the electronics connection substrate 50 comprises a flexible printed circuit board, as shown in FIGS. 13A-13F, configured to couple to and/or be compliant with an internal surface of the first housing portion 141, during manufacturing of the control module 130, and includes a set of electrical contact pads 52, each coupled to a conductive lead for signal transmission to the electronics subsystem 160, by way of the linking interface 55. However, variations to the flexible printed circuit board (e.g., a substrate produced using laser direct structuring, a substrate produced using two-shot molding) can be used as an electronics connection substrate 50.

The set of electrical contact pads 52 function to receive and route signals from the set of contacts 150 to the electronics subsystem 160. As such, the set of electrical contact pads 52 are preferably composed of a conductive material, and are preferably configured to couple to the set of contacts 150 in a manner that enables signal routing in a robust manner (e.g., without any cross-contact). Each electrical contact pad 52 can be composed of the same material; however, in some variations, one or more electrical contact pads in the set of electrical contact pads 52 can alternatively be composed of a different material than other electrical contact pads in the set of electrical contact pads 52. In a specific example, each electrical contact pad in the set of contact pads 52 includes a copper pad, which has suitable conductivity characteristics for signal transmission. However, variations of the specific example can comprise any other suitable material.

In coupling the set of electrical contact pads 52 to the set of contacts 150, at least one electrical contact pad can have an associated port 54 (e.g., an opening though the thickness of the electronics connection substrate), that functions to receive at least a portion of a second region 152 of a contact of the set of contacts 150. As such, the second region 152 of a contact can be mechanically retained in position at a corresponding electrical contact pad, by way of the port 54, in order to ensure robust coupling for reliable signal conduction through the contact. In one variation, the port 54 can be concentrically aligned with a corresponding electrical contact pad; however, the port 54 can alternatively be not concentrically aligned with the corresponding electrical contact pad. Furthermore, an electrical contact pad can have a single associated port, or multiple associated ports. Additionally or alternatively, the port 54 may not provide access entirely through the thickness of the electronics connection substrate 50.

Figure 13A:
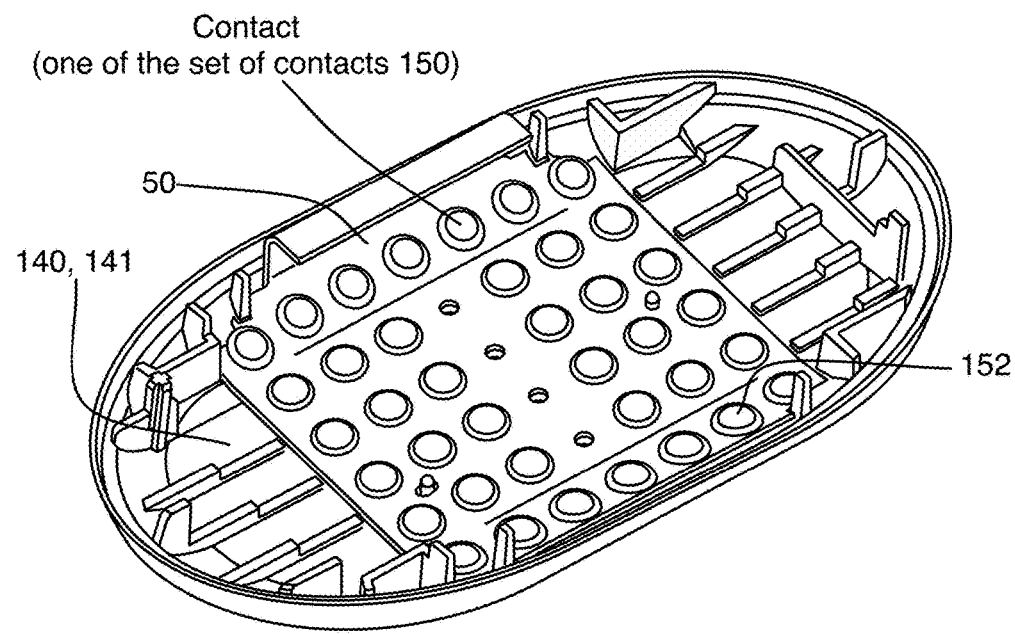
FIGS. 13A-13F depict schematics of a variation of a portion of a system for electrically coupling an exterior surface of a housing to an interior volume within the sealed housing.
Figure 13B:
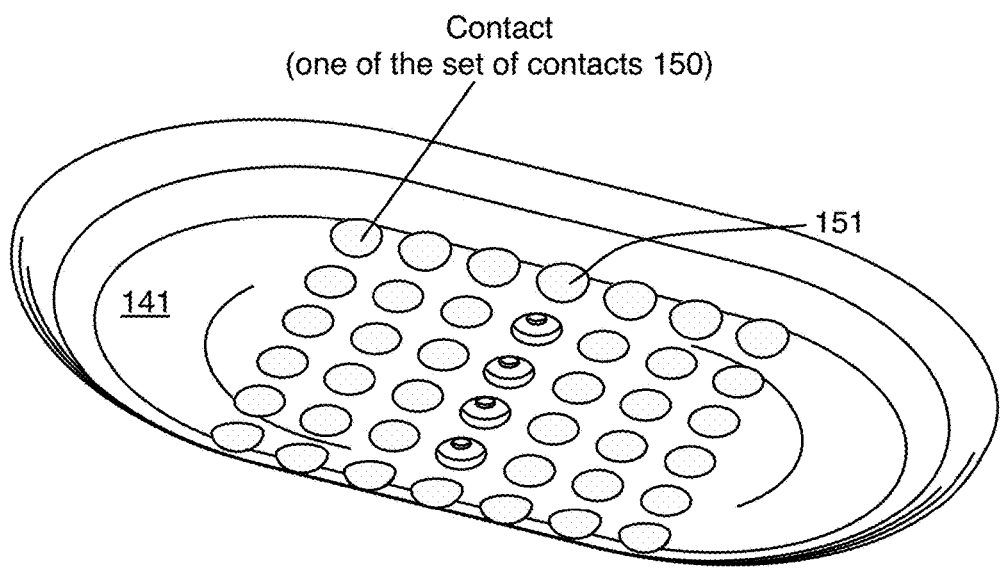
Figure 13C:
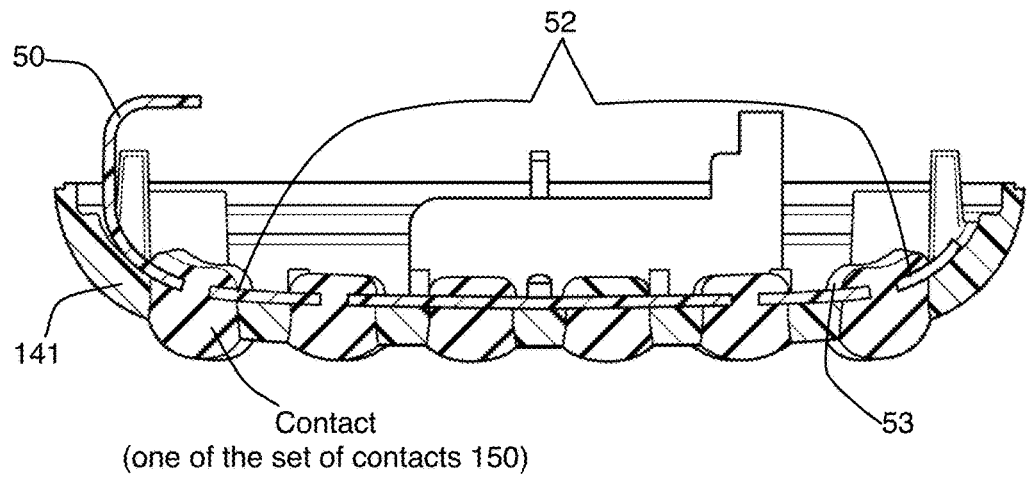
Figure 13D:
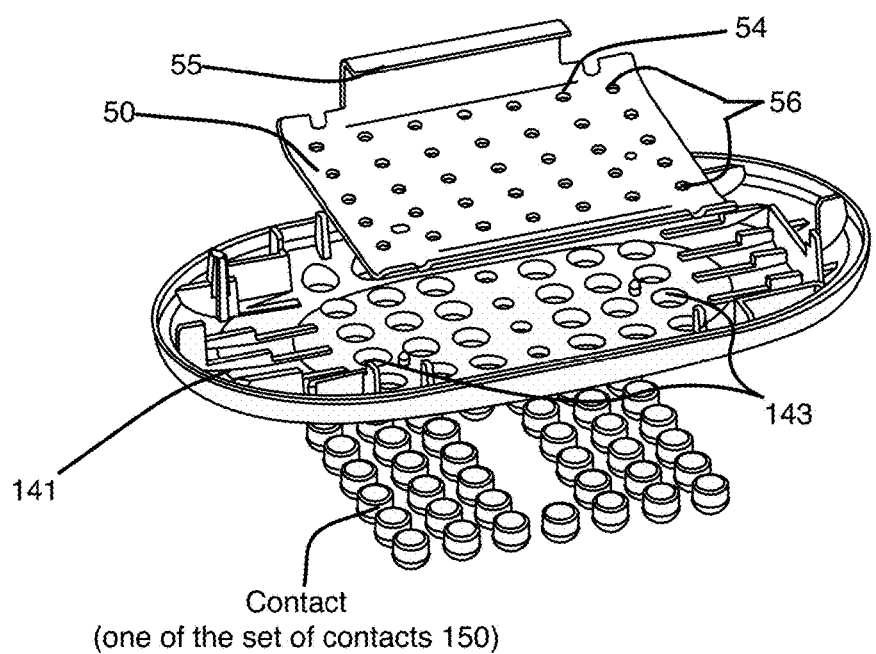
Figure 13E:
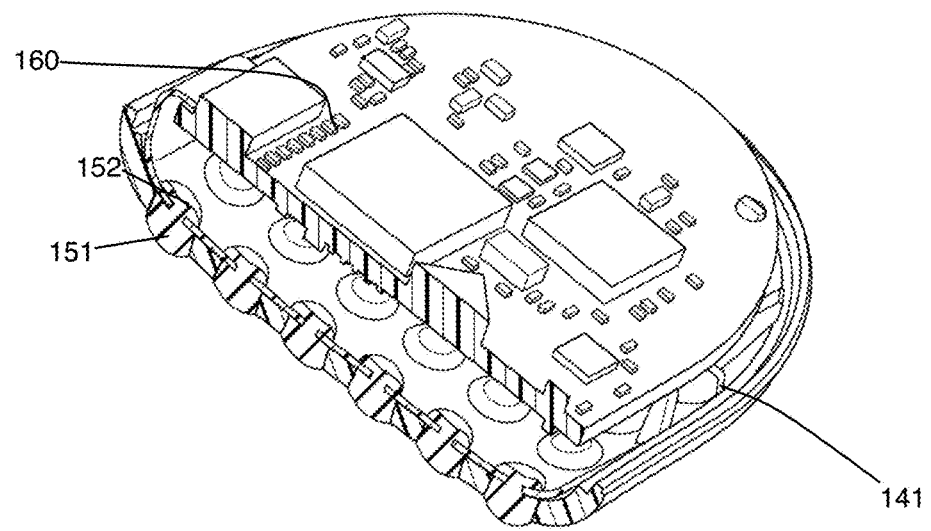

In relation to the set of electrical contact pads 52, the electronics connection substrate 50 is preferably configured such that the set of electrical contact pads 52 is paired with a set of ports 56, wherein the set of ports 56 is configured to align with the array of openings 143 of the housing 140. As such, and similar to the array of openings 143, the set of ports 56 can comprise a rectangular array of ports (i.e., with ports of the array of ports 56 arranged in a rectangular grid pattern) associated with the set of electrical contact pads, as shown in FIG. 13D; however, the set of ports 56 can alternatively be configured in any other suitable manner (e.g., as a circular array of ports, as an ellipsoidal array of ports, as a polygonal array of ports, as an amorphous array of ports, etc.). Each port 54 in the array of ports 56 can be a circular opening or can alternatively be a non-circular opening. Furthermore, each opening in the set of ports 56 is preferably identical to every other port in the set of ports 56 in morphology; however, the set of ports 56 can alternatively comprise non-identical openings. In a specific example, as shown in FIG. 13D, the set of ports 56 includes 42 identical circular openings arranged in a 7×6 rectangular array, such that the set of ports 56 aligns with and substantially matches the configuration of the array of openings 143 of the housing 140. However, the set of ports 56 can alternatively be configured in any other suitable manner.

Figure 13F:
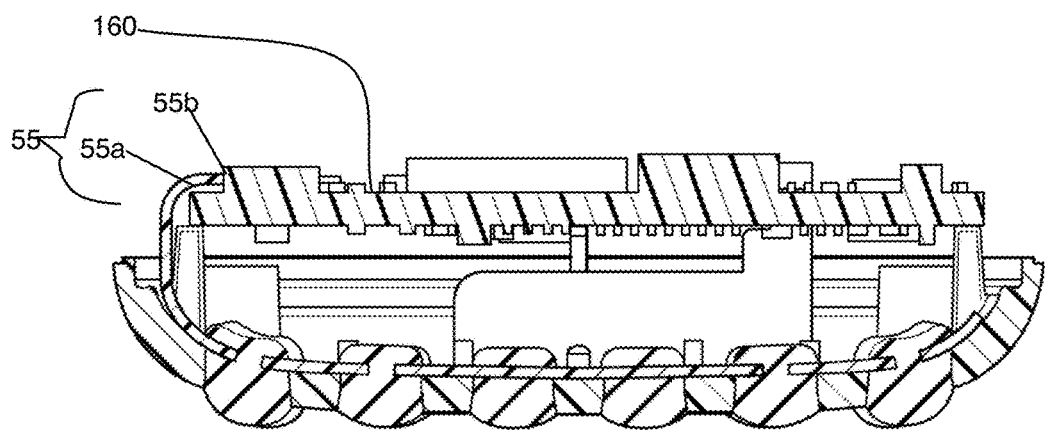

The linking interface 55 functions to transmit signals from the set of electrical contact pads 52 to the electronics subsystem 160 (as described in further detail below). The linking interface 55 is preferably a modular component of the control module 130 in order to facilitate assembly and manufacture of the control module 130. As such, the linking interface 55 can be configured to be in a disconnected state during some phases of manufacture of the control module 130, and to be in a connected state during final phases of manufacture of the control module. As such, in some variations, a first portion of the linking interface 55 can be coupled to (e.g., contiguous with) the electronics connection substrate 50, and a second portion of the linking interface 55 can be coupled to (e.g., contiguous with) the electronics subsystem 160. However, the linking interface 55 can alternatively be non-modular and coupled between the electronics connection substrate 50 and the electronics subsystem 160 in any other suitable manner. For instance, the electronics subsystem 160 can be contiguous with the electronics connection substrate 50, without a modular linking interface 55. In a specific example, as shown in FIG. 13F, the linking interface 55 comprises a first flexible printed circuit (FPC) connector 55a contiguous with the electronics connection substrate 50 and in communication with each electrical contact pad of the electronics connection substrate, wherein the first FPC connector 55a is configured to couple to a second FPC connector 55b of the electronics subsystem 160. However, variations of the specific example can comprise any other suitable configuration of the linking interface 55.

In relation to the configuration of the set of contacts 150, the contacts can each be assigned to and facilitate signal reception from a corresponding biometric sensor of the set of biometric sensors 120. Additionally, in some configurations, each contact and biometric sensor can be associated with a companion contact and biometric sensor to facilitate detection of a signal differential (i.e., a biopotential difference) across two paired biometric sensors. As such, the control module 130 can utilize signals from paired sensors in measuring a biopotential difference, thereby enabling determination of one or more metrics associated with muscle/exercise activity. In a first variation, the set of contacts 150 can be arranged according to pins on corresponding circuitry of the electronics subsystem 160. In the first variation, as shown in FIG. 5A, the set of contacts 150' can be arranged in a symmetrically opposing arrangement about any suitable axis of symmetry (e.g., a diagonal axis of symmetry defined by the array of openings 143 of the housing, a horizontal axis of symmetry defined by the array of openings 143 of the housing, a vertical axis of symmetry defined by the array of openings 143 of the housing, etc.). In an example of the first variation, contact 1A, as shown in the top left corner of the set of contacts shown in FIG. 5A, can be paired with contact 1B in the bottom right corner of the set of contacts 150, in facilitating detection of a first biopotential difference determined from two paired biometric sensors. In the example, the set of contacts 150 further comprises contacts associated with paired heart rate/respiratory signal detection sensors, ground pins of the electronics subsystem 160, and identification pins of the electronics subsystem 160.

Figure 6:
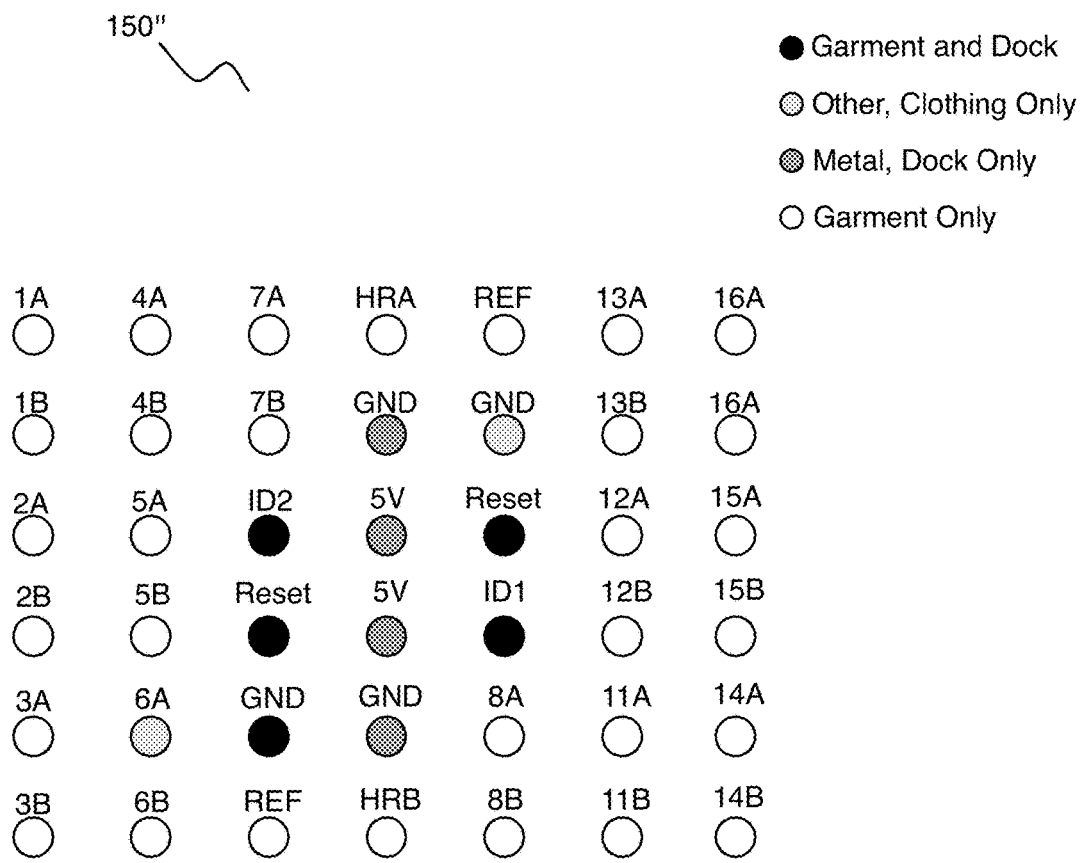
FIG. 6 depicts a second example configuration of contacts in an embodiment of a system for monitoring biometric signals of a user.

In a second variation, as shown in FIG. 6, the set of contacts 150" can be arranged such that associated pairs of contacts are positioned proximal to each other. In an example of the second variation, contact 1A, as shown in the top left corner of the set of contacts shown in FIG. 6, can be paired with contact 1B just below contact 1A (in the orientation shown in FIG. 6), in facilitating detection of a first biopotential difference determined from two paired biometric sensors. In the example, the set of contacts 150 further comprises contacts associated with paired heart rate/respiratory signal detection sensors, ground pins of the electronics subsystem 160, and identification pins of the electronics subsystem 160.

Variations of the first and the second variations of contact configurations can comprise any other suitable combination of symmetrically opposing arrangements of paired contacts and proximal placement of paired contacts. For instance, a portion of paired contacts associated with biometric sensors can be proximally placed, while other contacts (e.g., contacts associated with identification pins, contacts associated with ground pins, etc.) can be arranged in a symmetrically opposing arrangement.

In any of the above contact configurations, and for control modules 130 with housings 140 that can be coupled with the garment 105 in multiple orientations (e.g., for a control module 130 that has a housing 140 with at least one axis of symmetry), the control module can be configured to utilize the contact configuration(s) and any other suitable data (e.g., accelerometer data, gyroscope data) in order to detect the orientation of the control module relative to the garment 105, and to adapt signal reception and processing functions accordingly. As such, the control module 130 can be configured to operate properly regardless of how the control module is coupled with the garment 105. Thus, a user would not need to ensure that the control module 130 is coupled with the garment 105 according to a specific orientation (e.g., based upon alignment marks on the control module, based upon asymmetry of the control module, etc.). Additionally, the control module 130 and contact configurations can have associated components (e.g. integrated circuits, field programmable gate arrays, multiplexors, resistors, etc.) and/or firmware to facilitate correct mapping between the set of contacts 150 and the set of biometric sensors 120 in a desired manner. For example, using the contact configuration shown in FIG. 6, signals X and Y can be received by way of contacts 1A and 1B in a first orientation of the control module 130, but if the control module is positioned "upside-down" in a second orientation, firmware can adapt signal reception and processing of the control module to receive signals X and Y by way of contacts 14B and 14A, respectively. As such, in the example, the control module 130 can be configured to dynamically modify the contact mapping in order to property attribute signals X and Y to the correct muscle group or set of biometric sensors. Alternatively, the control module 130 and/or housing 140 can be configured to couple with the garment 105 in only a single orientation (e.g., based upon markings, based upon asymmetry in the control module 130 or housing, etc.), such that the control module 130 does not require firmware that enables adaptive coupling.

Figure 14:
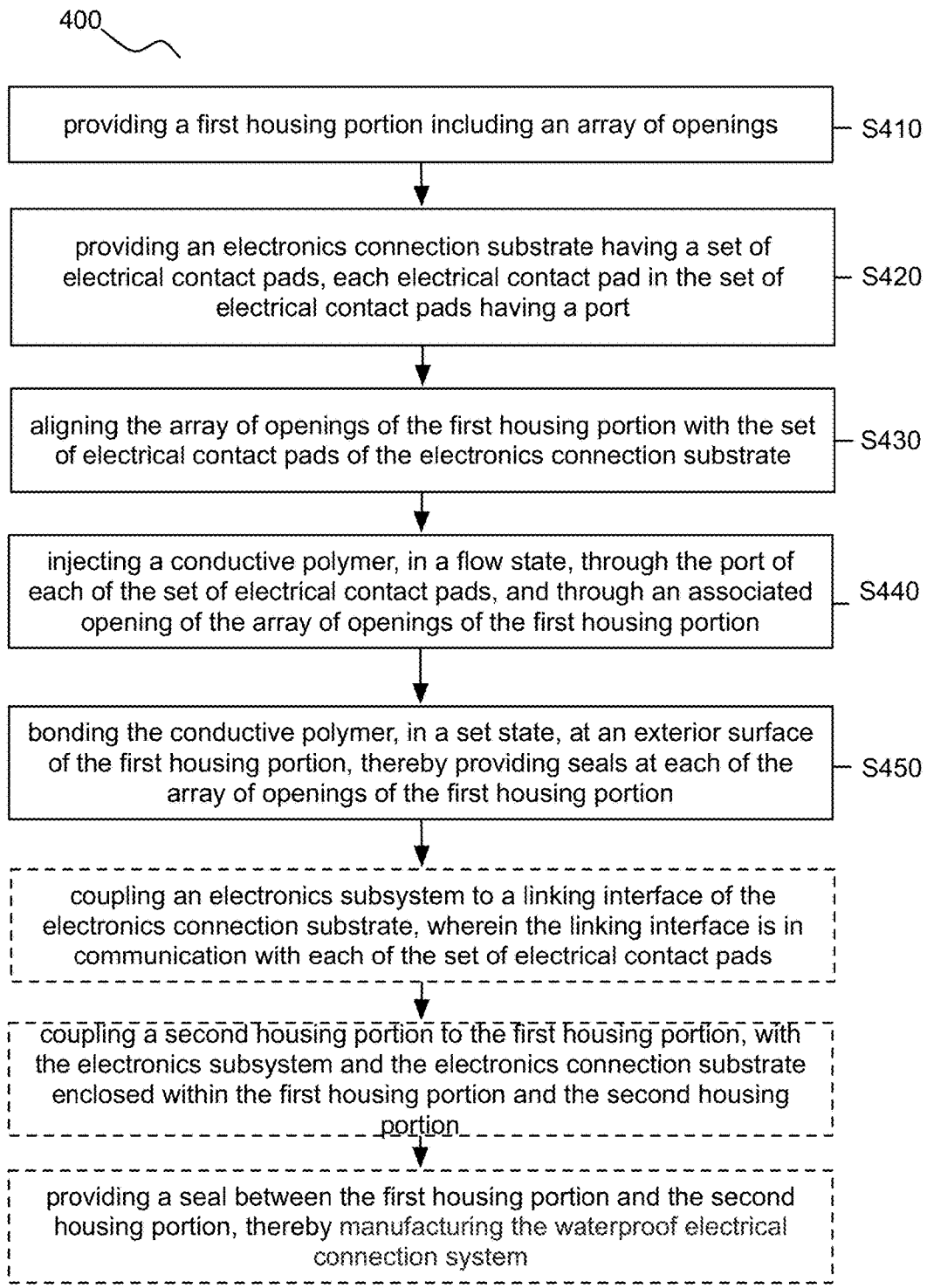
FIG. 14 depicts an embodiment of a method for fabricating signal conduction pathways in a waterproof manner, in an embodiment of a system for monitoring biometric signals of a user.

1.2.2 Control Module—Housing, Contacts, and Electronics Connection Substrate Manufacture and Assembly As shown in FIG. 14, and in relation to manufacture of the control module 130 and/or similar electronic interfaces, a method 400 of manufacturing a waterproof electrical connection system includes: providing a first housing portion including an array of openings S410; providing an electronics connection substrate having a set of electrical contact pads, each electrical contact pad in the set of electrical contact pads having a port S420; aligning the array of openings of the first housing portion with the set of electrical contact pads of the electronics connection substrate S430; injecting a conductive polymer, in a flow state, through the port of each of the set of electrical contact pads, and through an associated opening of the array of openings of the first housing portion S440; and bonding the conductive polymer, in a set state, at an exterior surface of the first housing portion, thereby providing seals at each of the array of openings of the first housing portion S450. Variations of the electronics connection substrate can, however, include one or more electrical contact pads that omit a port, as discussed in relation to the system of Section 1.2.1 above.

The method 400 functions to produce a system for signal communication, wherein the system has conductive contacts on an exterior surface of a housing, and provides a signal conduction pathway to one or more elements interior to the housing. In particular, the method 400 can provide waterproof conductive contacts at the exterior surface of the housing, which transmit signals to electronics housed within the housing. In variations and examples, the method 400 can be used in manufacture and assembly of the control module 130 described above and below; however, the method 44 can additionally or alternatively be used to facilitate manufacture of any suitable wearable electronic device or non-wearable electronic device, wherein signal transmission from an exterior surface of a housing to electronics interior to the housing, in a substantially waterproof (e.g., water resistant to a high degree) is needed.

Block S410 recites: providing a first housing portion including an array of openings, which functions to provide a first portion of the waterproof system that provides coupling regions for a set of conductive contacts. The first housing portion also functions to provide a waterproof enclosure around electronic components of the system, in protecting them from damage. In embodiments, variations, and examples, the first housing portion is preferably the first housing portion described in Section 1.2.1 above, which has an array of openings configured to be sealed (e.g., sealed in a water tight manner) by a set of contacts; however, in other variations, the first housing portion can comprise any other suitable enclosure configured to enclose at least a portion of electronics of the system and/or couple to the set of contacts.

Block S420 recites: providing an electronics connection substrate having a set of electrical contact pads, each electrical contact pad in the set of electrical contact pads having a port. Block S420 functions to provide a second portion of the waterproof system that provides coupling regions for a set of conductive contacts. The electronics connection substrate also functions to route signals from the set of contacts, through electrical contact pads, to an electronics subsystem by way of a linking interface, as described in Section 1.2.1 above. In embodiments, variations, and examples, the electronics connection substrate is preferably the electronics connection substrate described in Section 1.2.1 above, which has a set of electrical contact pads and an associated set of ports configured to align with the array of openings of the first housing portion, and configured to couple to the set of contacts; however, in other variations, the electronics connection substrate can comprise any other suitable substrate configured to couple to the set of contacts and route signals from the set of contacts to the electronics subsystem.

Figure 15A:
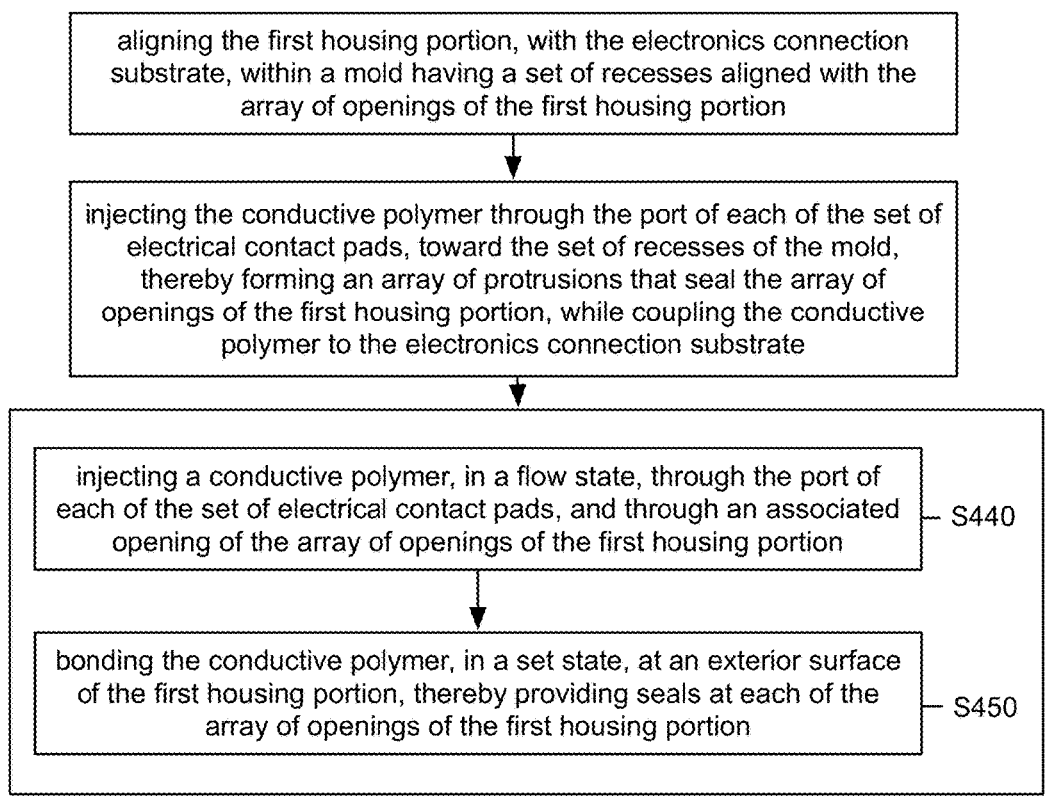
FIGS. 15A-15D depict variations of a method for fabricating electrical conduction pathways in a waterproof manner, in an embodiment of a system for monitoring biometric signals of a user.

Block S430 recites: aligning the array of openings of the first housing portion with the set of electrical contact pads of the electronics connection substrate, which functions to position the first housing portion and the electronics connection substrate in a configuration that allows for transmission of the material of the set of contacts, through the electronics connection substrate and the first housing portion, in Block S440. Block S430 preferably includes aligning the first housing portion and the electronics connection substrate, with the array of openings of the housing aligned with the set of ports of the electronics connection substrate, within a mold, as shown in FIG. 15A. Preferably, the mold is configured for injection molding of the conductive material of the set of contacts through at least one of the set of ports and the array of openings, in Block S440; however, the mold of Block S430 can alternatively be suited for alignment only, with another mold or device used to facilitate injection molding in Block S440. In still other variations, the mold used in Block S430 can be used for alignment in relation to any other suitable process (e.g., extrusion, press fitting, riveting, etc.) involving coupling of the set of contacts to the first housing portion and the electronics connection substrate, in a waterproof manner. For instance, a mold for alignment can be used in an extrusion process, wherein waterproof seals at interfaces between the set of contacts and the first housing portion/electronics connection substrate are generated using sealing elements (e.g., o-rings, x-rings, primers, sealing putty, etc.). Additionally or alternatively, one or more of the set of contacts can be pre-constructed and applied (e.g., press-fit, etc.) into the corresponding opening(s) of the first housing portion. In one related variation, the set of contacts can be pre-constructed and coupled to a disposable substrate, wherein, after applying the set of contacts into the corresponding opening(s) of the first housing portion, portions of the disposable substrate can be uncoupled from the set of contacts (e.g., by cutting, by tearing, etc.).

In a specific example, as described in FIG. 15A, a mold used in Blocks S430 and S440 includes a set of recessed regions (e.g., hemispherical recessed regions) aligned with the array of openings of the housing, wherein the set of recessed regions receive injected material in Block S440, and form protrusions at the exterior surface of the housing, in correspondence with the array of openings of the first housing portion. The set of recessed regions of the mold of the specific example thus correspond in a one-to-one manner with the array of openings of the first housing portion. As such, the set of recessed regions guide formation of the first region of each contact (i.e., the portion of each contact at the exterior surface of the housing), in a consistent manner, without bridging of contacts. However, variations of the mold of the specific example can omit recessed regions, can include recessed regions having any other suitable morphology (e.g., recessed pyramidal regions), can include recessed regions having any suitable relationship (e.g., in number, in overlap) with the array of openings of the first housing portion, or can additionally or alternatively be configured to guide formation of any other suitable portion of the set of contacts (e.g., the second region of a contact, at the electronics connection substrate).

Figure 15B:
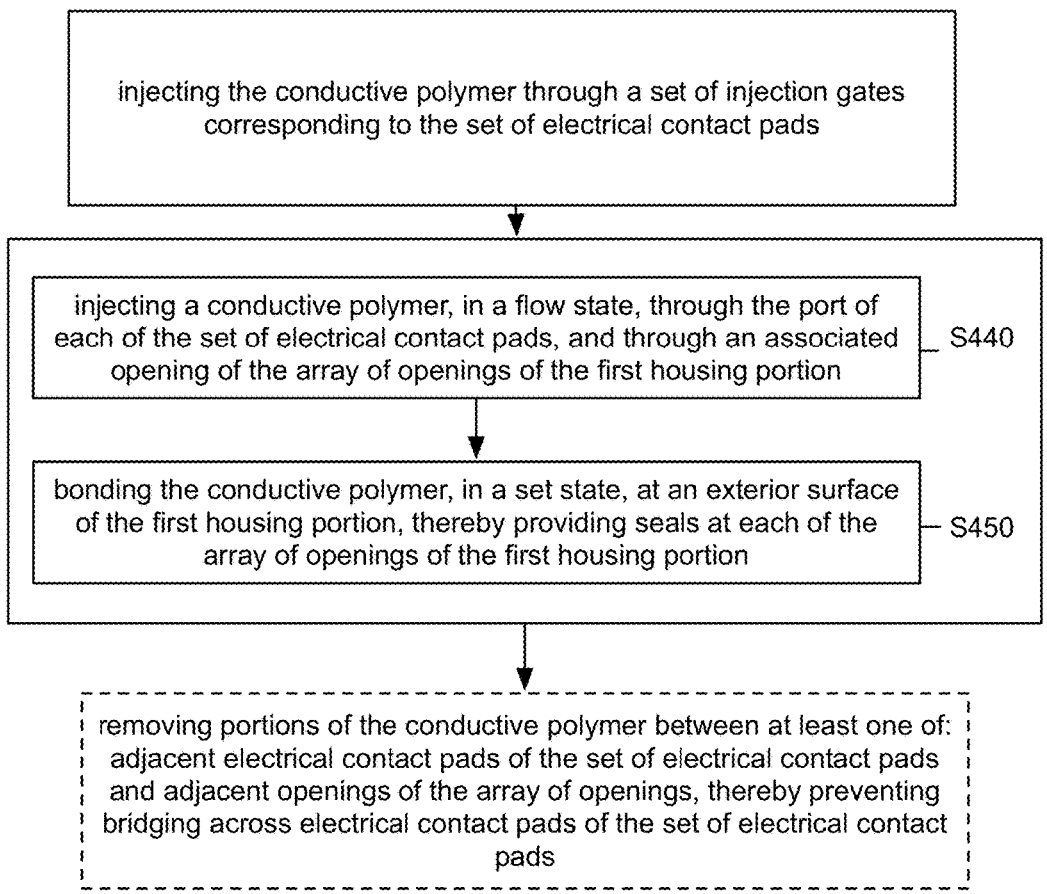

Block S440 recites: injecting a conductive polymer, in a flow state, through the port of each of the set of electrical contact pads, and through an associated opening of the array of openings of the first housing portion, and Block S450 recites: bonding the conductive polymer, in a set state, at an exterior surface of the first housing portion, thereby providing waterproof seals at each of the array of openings of the first housing portion. Blocks S440 and S450 function to transmit conductive polymer material of the set of contacts, in a manipulatable form, through the ports of the electronics connection substrate and the openings of the first housing portion, in a manner that provides a waterproof interface at the exterior of the housing, while still enabling signal transmission into an interior portion of the housing. As such, the result of Blocks S440 and S450 is to produce conductive contacts that are coupled to electrical contact pads of the electronics connection substrate (i.e., without cross-contact shorting), while forming a waterproof seal at the external surface of the first housing portion. In one variation, conductive polymer (e.g., conductive ether-based thermoplastic polyurethane) is injected into the set of ports of the electronics connection substrate. In this variation, the conductive polymer can be injected into all ports simultaneously, or can alternatively be injected into subsets of the set of ports in stages. As such, and as shown in FIG. 15B, in injecting the conductive polymer through the set of ports, each port can have its own associated injection gate, in order to prevent shorting of individual electrical contact pads of the electronics connection substrate. Alternatively, all desired regions can be injection molded simultaneously, with subsequent removal of material that would otherwise undesirably connect electrical contact pads. Furthermore, in this variation, the conductive polymer is injected in a manner that originates at the set of ports, and terminates at the exterior surface of the first housing portion, by way of the array of openings of the first housing portion and the set of recesses of the mold used during injection molding (as described above).

Figure 15C:
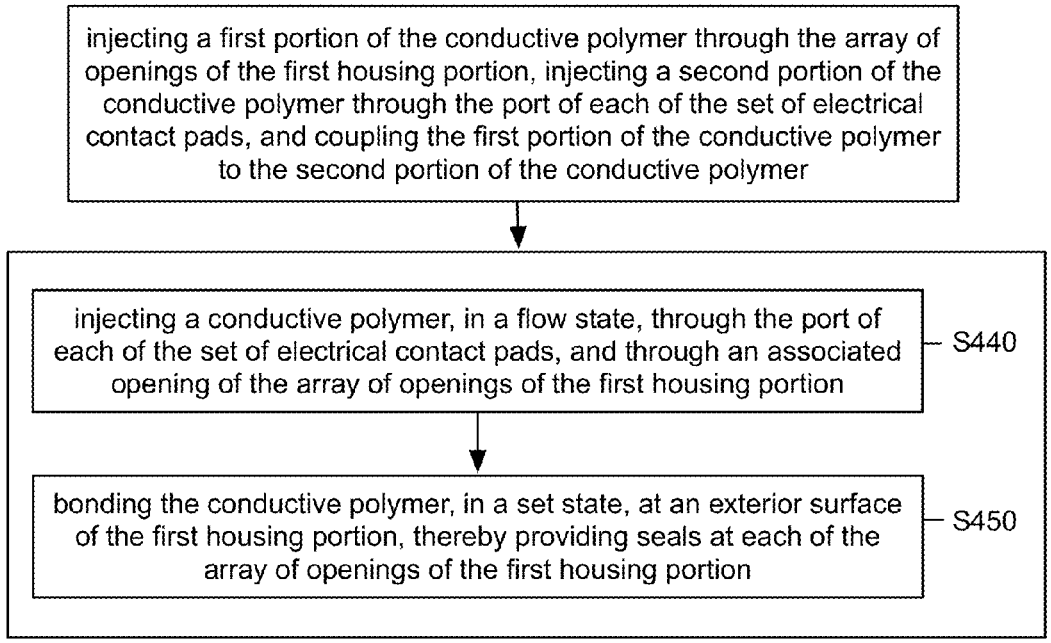

While this variation of Blocks S440 and S450 describes injection of conductive polymer material through the set of ports, with termination at the exterior portion of the first housing portion, alternative variations of Block S440 can include injection of conductive polymer material in a reverse direction (e.g., from the exterior surface of the housing, with termination at the set of electrical contact pads of the electronics connection substrate). In still alternative variations, a contact can be formed in two parts by way of Blocks S440 and S450, with a first part formed initially at the first housing portion, and a second part formed at the electronics connection substrate (e.g., in association with an electrical contact pad). Blocks S440 and S450 can then include coupling of the first part to the second part (e.g., using a thermal bonding process, using a chemical bonding process, using an adhesive, using any other suitable coupling process), in order to allow signal communication from the first part of the contact to the second part of the contact, as described in FIG. 15C.

Figure 15D:
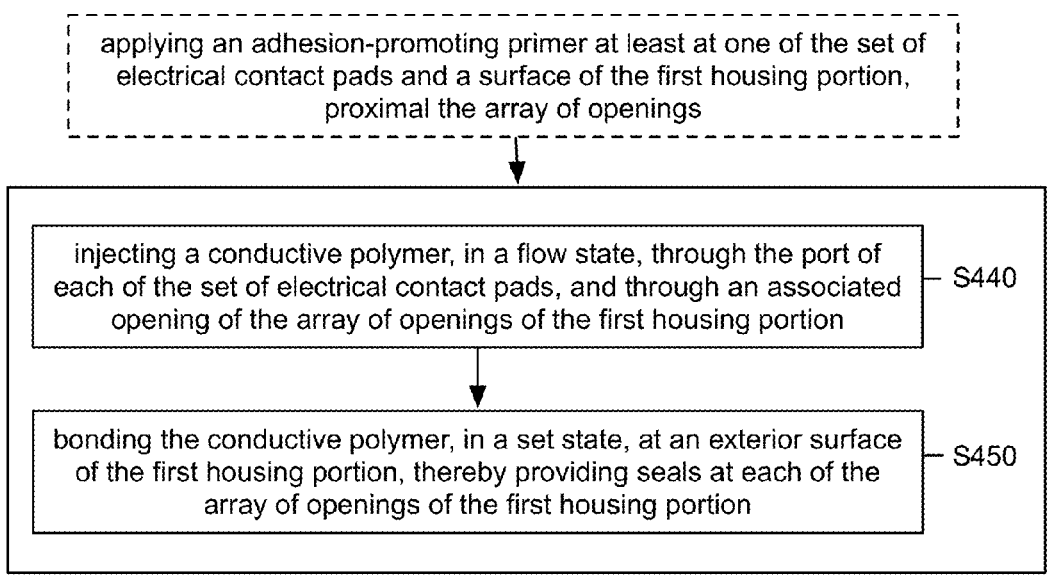

In Blocks S440 and S450, suitable electrical coupling between the conductive polymer of the set of contacts and the electrical contact pads of the electronics connection substrate can be provided based upon mechanical coupling alone. However, Blocks S440 and S450 can additionally or alternatively include implementing an adhesion-promoting primer at the set of electrical contact pads of the electronics connection substrate, as described in FIG. 15D, which can further enhance electrical coupling between a contact and an electrical contact pad. The adhesion-promoting primer is preferably conductive in order to not interfere with signal communication across the electrical contact pads; however, any other suitable material or process can be used to promote robust coupling between the set of contacts and the electrical contact pads of the electronics connection substrate. In one variation, and in relation to Block S440, the method 400 can thus include applying an adhesion-promoting primer at each electrical contact pad (e.g., at any surface associated with a port) of the electronics connection substrate, prior to injection molding of the conductive polymer through the set of ports. However, variations of Block S440 that implement an adhesion-promoting primer can alternatively be performed in any other suitable manner.

Similarly, in Blocks S440 and S450, generation of a suitable waterproof or hermetic seal at the first housing portion can be provided based upon mechanical coupling alone. However, Blocks S440 and S450 can additionally or alternatively include implementing an adhesion-promoting primer at a surface of the first housing portion, proximal the array openings, which can further enhance coupling in a waterproof manner between a contact and the first housing portion. In one variation, and in relation to Block S450, the method 400 can thus include applying an adhesion-promoting primer at the first housing portion (e.g., at any surface associated with an opening), prior to injection molding of the conductive polymer. However, variations of Block S450 that implement an adhesion-promoting primer can alternatively be performed in any other suitable manner.

In relation to the control module of Section 1.2.1 above, the method 400 can then include any other suitable steps related to assembly of the control module. For instance, the method 400 can include one or more of: coupling the electronics connection substrate to the electronics subsystem; coupling a second housing portion to the first housing portion in a manner that provides a waterproof or hermetic seal at an interface between the first housing portion and the second housing portion (e.g., using an o-ring, using an x-ring, using sealing putty, using a water resistant adhesive, using a waterproof adhesive, etc.); and any other suitable step related to assembly of the control module, some variations of which are shown in FIG. 14.

While the above method 400 is described in relation to a set of contacts coupled to a housing and an electronics connection substrate in an improved manner, variations of the method 400 can be adapted to coupling of a single contact to a housing and/or an electronics connection substrate, in producing a waterproof system configured to transmit signals originating exterior to the housing, to elements interior to the housing.

1.2.3 Control Module—Other Elements

The electronics subsystem 160 is configured to be in electrical communication with the set of contacts 150, and functions to facilitate signal reception, signal conditioning, signal transmission, and power distribution for the system 100. The electronics subsystem 160 is preferably housed within an internal portion of the housing 140 of the control module 130, in order to be isolated from mechanisms that could damage the electronics subsystem 160; however, the electronics subsystem 160 can alternatively be configured in any other suitable manner. The electronics subsystem 160 preferably comprises a power module 161, a supplementary sensing module 163, a signal conditioning module 165, a communication interface 167, and memory 169; however, the electronics subsystem 160 can additionally or alternatively include any other suitable element(s) that add to and/or enrich acquired data and/or facilitate conditioning or processing of signals from the user as the user performs a physical activity.

The power module 161 of the electronics subsystem 160 functions to provide regulated and unregulated electrical power to the system 100 and to allow power storage for the system 100. The power module 161 preferably comprises a rechargeable battery 162 (e.g., a lithium-ion battery, nickel-cadmium battery, metal halide battery, nickel metal hydride battery, lithium-ion polymer battery, etc.); however, the power module 161 can alternatively comprise a non-rechargeable battery (e.g., alkaline battery) that can be replaced to further enhance modularity in the system 100. Additionally or alternatively, the power module 161 can include any other suitable element (e.g., super capacitor, solar cell, vibration-powered generator, thermoelectric generator, etc.). Preferably, the power module 161 is configured to have a profile with a low aspect ratio, contributing to a thin form factor of the control module 130/housing 140. However, the power module 161 can be configured to have any other suitable profile such that the power module 161 provides adequate power characteristics (e.g., cycle life, charging time, discharge time, etc.) for the system 100.

In variations where the battery 162 of the power module 161 is rechargeable, the electronics subsystem 160 can also comprise a coil of wire and associated electronics that function to allow inductive coupling of power between an external charging element 62 and the power module 161, as shown in FIGS. 1 and 9A-9B. The charging coil preferably converts energy from an alternating electromagnetic field (e.g., provided by a charging dock or other adapter), into electrical energy to charge the battery 162 and/or to power the system 100. Inductive charging allows electrical isolation between the external charging element 62 and internal electronics of the electronics subsystem 160 to promote user safety and convenience in interfacing with the system 100. Inductive charging provided by the charging coil thus also facilitates user mobility while the user interacts with the system 100, such that the user can perform a wide range of physical activities while having his/her biometric signals monitored by the system 100. In alternative variations, however, the charging coil can be altogether omitted (e.g., in variations without a rechargeable battery), or replaced or supplemented by a connection (e.g., USB connection) configured to provide wired charging of a rechargeable battery.

The supplementary sensing module 163 functions to facilitate acquisition of additional data from the user, which can be used to trigger control of aspects of signal acquisition and/or analysis generation by the control module 130. As such, not all sensors of the system 100 may be separate from the control module 130. The supplementary sensing module 163 preferably includes a set of supplementary sensors 164 configured to detect one or more aspects associated with motion of the user and/or an environment of the user. In variations, the set of supplementary sensors 125 can include one or more of: an accelerometer (e.g., a single axis accelerometer, a multi-axis accelerometer), a gyroscope (e.g., a single axis gyroscope, a multi-axis gyroscope), a GPS module, environmental temperature sensors, altimeters, oxygen content sensors, air quality sensors, near field communication (NFC) sensors (e.g., configured to detect a nearby device or piece of exercise equipment having a corresponding NFC element), and any other suitable supplementary sensor that can enrich the data acquired from user and/or the environment of the user. In one example, accelerometers of the supplementary sensing module 163 can be used to detect a type of physical activity (e.g., cardio exercise, weight training exercise, etc.) performed by the user, and/or can be used during signal processing to remove motion-produced artifacts from signals being processed. The supplementary sensing module 163 can, however, comprise any other suitable sensors and be configured relative to the electronics subsystem 160 in any other suitable manner.

The signal conditioning module 165 functions to preprocess signals detected and received using the set of biometric sensors and/or sensors of the supplementary sensing module 163, thereby producing conditioned data prior to processing. In variations, the signal conditioning module 165 can comprise elements configured to perform any one or more of: filtering (e.g., using a low pass filter, a high pass filter, a band-pass filter, a notch filter, etc.), smoothing, clipping, deconvolving, detrending/offsetting, standardizing, resampling, hard-binding, predicting, windowing, and any other suitable data conditioning process upon any signals received from the set of biometric sensors 120. The signal conditioning module can thus comprise one or more of: filters, amplifiers, analog-to-digital converters (ADCs), digital-to-analog converters (DACs), signal multiplexers, and any other suitable elements for conditioning signals received from biometric sensors and supplementary sensors.

The communication interface 167 preferably comprises hardware and/or software elements configured to facilitate communication of information between the set of biometric sensors 120 and the control module 130, and/or communication of information between the control module 130 and one or more separate devices (e.g., a processing subsystem, a mobile computing device of the user, etc.). As such, the communication interface 167 can function as a data link that provides a means for communications to and from the control module 130 over a network. The network can comprise any suitable network used for communication between electronic devices. The network can include a wireless and/or a wired connection between devices. In examples of wireless connections, the network associated with the communication interface 167 can include any one or more of: a local area network (LAN), a wireless LAN (WLAN), a Bluetooth network (e.g., a Bluetooth Low Energy network), a municipal area network (MAN), a wide area network (WAN), the internet, and any other suitable network. Furthermore, in some variations, the communication interface 167 can include features that provide security in information communication. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

In wired variations of the communication interface 167, the communication interface can implement any one or more of an audio jack connection (e.g., AUX cable), a USB connection, a parallel port, a serial port, an ethernet adapter, an IEEE 1394 bus interface, a small computer system interface (SCSI) bus interface, an infrared (IR) communication port, and any other suitable wired or hardware connection. In this variation, the communication interface 167 can communicate with other devices over a network using one or more of: inter-integrated circuit communication (I2C), one-wire, master-slave, or any other suitable communication protocol. However, the communication interface 167 can transmit data in any other way and can include any other type of wired connection that supports data transfer between the electronics subsystem 160, external devices, and/or any other suitable computing element.

The memory 169 functions to retain data from signals received at the electronics subsystem 160. As such, upon receiving signals from the set of biometric sensors 120, the electronics subsystem 160 of the control module 130 can thus facilitate storage of biometric data (e.g., conditioned data from biopotential signals, unconditioned data from biopotential signals) within memory of the electronics subsystem 160. The memory 169 can comprise processor-readable medium including any one or more of: random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and any other suitable storage element. Preferably, data from the memory 169 is automatically transmitted to any appropriate external device, over a network, substantially continuously (e.g., every second, every millisecond, etc.); however, data from the data storage unit 180 can alternatively be transmitted intermittently (e.g., every minute, hourly, daily, or weekly). In one example, data generated by any element of the system 100 may be stored in memory 169 when the communication interface 167 is not actively coupled to an element external to the electronics subsystem 160 over the network. However, in the example, when a link is established between the communication interface 167 and an external element, data may then be automatically transmitted from memory 169. In other examples, the memory 169 can additionally or alternatively be manually prompted to transmit stored data, when prompted by a user or other entity.

Figure 12:
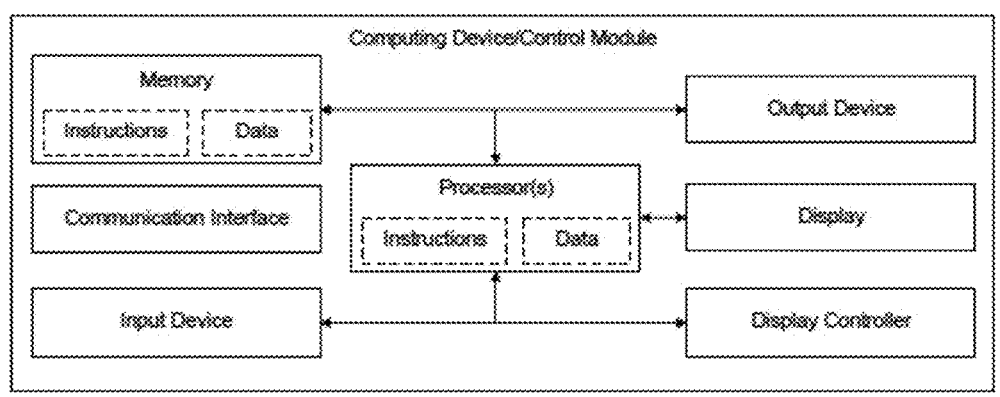
FIG. 12 depicts an embodiment of a portion of a system for monitoring biometric signals of a user.

The control module 130 can, however, include any other suitable elements, including input devices (e.g., keyboard, mouse, microphone, remote control, button, joystick, trackball, touchpad, optical sensor), wherein the input device(s) can receive input from another device, and output devices (e.g., displays, projectors, speakers, tactile devices, network cards, wireless transmitters, infrared transmitters, lights, etc.) that convey information to a user, as shown in FIG. 12. For instance, an output device associated with the control module 130 can display a graphical user interface (GUI) that facilitates user interaction. Such a display can utilize any suitable image projection technology, such as a cathode ray tube (CRT), liquid crystal display (LCD), light-emitting diode (LED), gas plasma, electroluminescence, or any other suitable image projection technology.

1.3 System—Mounting Module

Figures 7A, 7B:
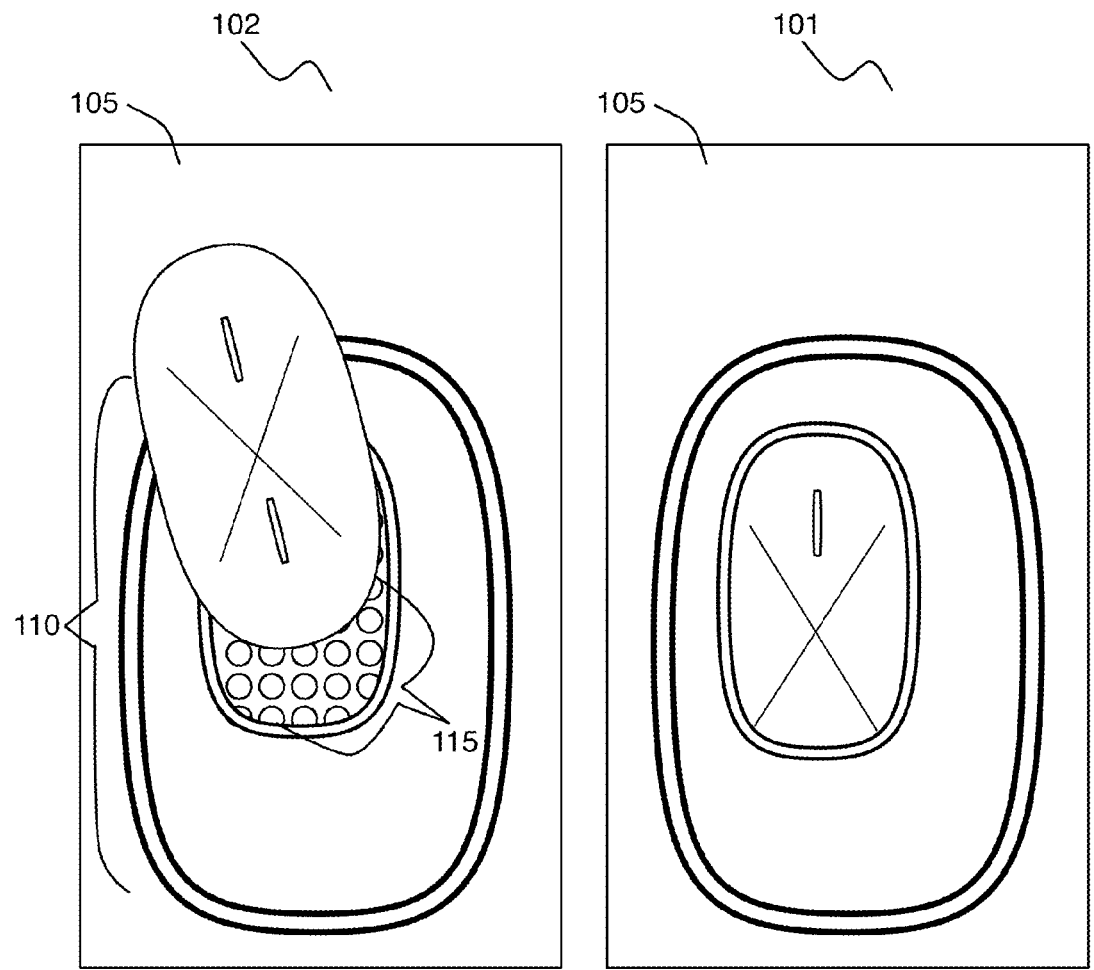
FIGS. 7A-7B depict a first configurations and a second configuration, respectively, of coupling between a control module and an array of connection regions in an embodiment of a system for monitoring biometric signals of a user.

In relation to coupling between the control module 130 and the garment 105, the system 100 can also include a mounting module 110, as shown in FIGS. 7A and 7B, that receives the control module 130 in order to facilitate coupling of the control module 130 to the garment 105 in a reversible and repeatable manner. The mounting module 110 thus preferably provides an array of connection regions 115, which function to facilitate electrical coupling between the set of biometric sensors 120 and the set of contacts 150 of the control module 130 in a first configuration 101. As such, the garment 105 can also function to serve as a substrate for facilitating electrical coupling between the set of biometric sensors and the mounting module 110. In variations, the mounting module 110 and/or the garment 105 can include any one or more of: slots, pouches, ports, bases, pathways, channels, cradles, and any other suitable feature by which the set of biometric sensors and/or control module 130 can be permanently or removably coupled to each other and/or to the mounting module 110 or the garment 105. Furthermore, the garment 105 can include conductive leads (e.g., wires, conductive filaments) passing along and/or throughout the garment 106 to enable signal transmission between the mounting module 110 and the set of biometric sensors 120 (e.g., by way of the plurality of conductive regions 106 of the garment 105). Alternatively, the garment 105 or any other element of the system 100 can be configured to facilitate wireless communication between the set of biometric sensors 120 and the control module 130. In one such example, the garment 105 and other elements of the system 100 can be configured according to an embodiment, variation, or example described in U.S. Application No. 62/077,781, entitled "Biometric Monitoring Garment" and filed on 10 Nov. 2014.

The mounting module 110 thus functions to provide an electrical and mechanical interface between the control module 130 and the set of biometric sensors 120 of the garment 105, in facilitating signal transmission in a robust manner as the user performs a physical activity. In producing a robust electrical and mechanical interface, the mounting module 110 can comprise a set of layers 111 coupled to each other and/or to a surface of the garment 105, wherein the set of layers provide a biasing force that maintains contact between the set of contacts 150 of the control module and the array of connection regions 115 of the mounting module 110. In generating the biasing force, the set of layers 111 can include one or more of elastic layers (e.g., elastic fabrics), compliant layers (e.g., foam layers), and substantially rigid layers (e.g., layers that are configured to accommodate the control module 130 in a press-fit or snap-fit manner). As such, the mounting module 110 provides a robust electro-mechanical connection between the control module 130 and the array of connection regions 115 of the mounting module 110 in a first configuration 101, and enables decoupling of the control module 130 from the mounting module 110 in a second configuration.

Figure 8A:
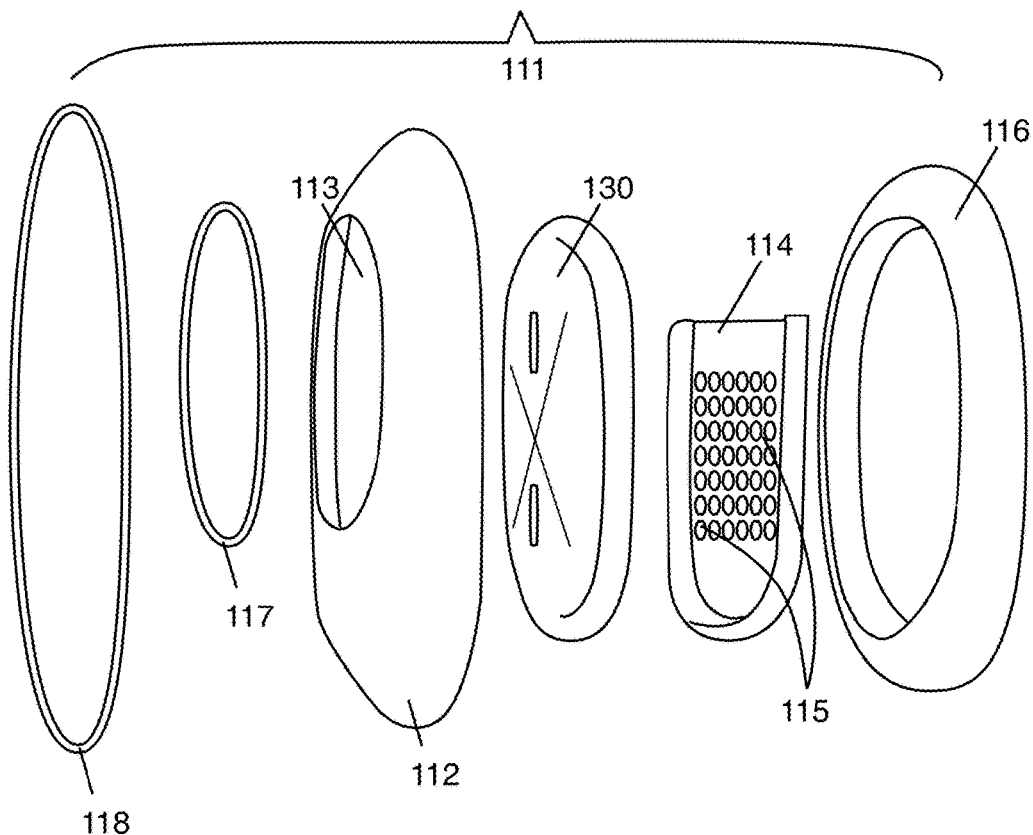
FIG. 8A depicts an example of a mounting module in an embodiment of a system for monitoring biometric signals of a user.

In one example, as shown in FIG. 8A, the mounting module 110 comprises: a fabric layer 112 affixed to the garment 105 and defining a receiving pocket for the control module 130, wherein the fabric layer 112 has an elastic opening 113 that accommodates reception of the control module 130 and exposes one or more indicator LEDs of the control module 130; a cradle 114 deeper than the fabric layer 112 and comprising the array of connection regions 115 that couple to the set of biometric sensors 120; a foam ring 116 at least partially surrounding the cradle 114 and deeper than the fabric layer 112, wherein the foam ring 116 functions to provide stability to a control module 130 seated within the fabric layer 112 at the cradle 114, and can further function to protect the user from the rigidity of the cradle as well as shielding regions where sensor leads are coupled to the cradle 114; a first tape ring 117 surrounding at least a portion of the elastic opening 113 of the fabric layer 112; and a second tape ring 118 surround at least a portion of the periphery of the fabric layer 112, wherein the first tape ring 117 and the second tape ring 118 function to provide structural integrity to the fabric. The mounting module 110 can, however, comprise a configuration such as that described in U.S. Provisional Application Ser. No. 62/013,405 filed 17 Jun. 2014, and/or U.S. Provisional Application Ser. No. 62/016,373 filed 24 Jun. 2014, both entitled "Biometric Monitoring System". Additionally or alternatively, variations of the mounting module 110 can comprise combinations of any of the above variations and examples, or any other suitable configuration of a mounting module.

Figure 8B:
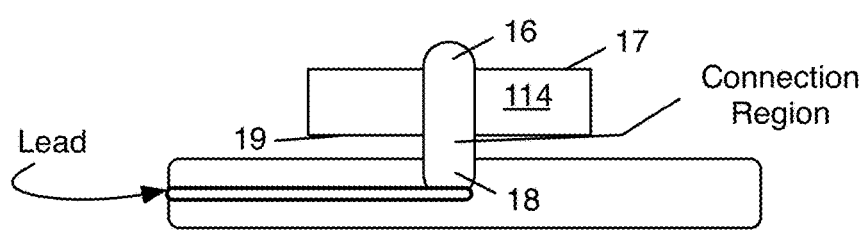
FIG. 8B depicts a cross section of a portion of an embodiment of a system for monitoring biometric signals of a user.

In the example, and with regard to the cradle 114, the cradle 114 is preferably composed of a rigid material (e.g., rigid plastic) having the array of connection regions 115 arranged in a configuration that is complementary to the set of contacts 150 of the control module 110. As such, in the example, the array of connection regions 115 comprises a 7×6 array of circular connection regions configured to couple with the 7×6 array of circular contacts of the control module 130. In the example, each connection region of the array of connection regions 115 comprises a conductive silicone rubber; however, the connection regions can additionally or alternatively be composed of any other suitable material. Similar to the set of contacts 150, and as shown in FIG. 8B, each connection region in the array of connection regions can have a first region 16, exposed through a first cradle surface 17 configured to contact the first region 151 of at least one contact, and a second region 18 in communication with the first region 16 and configured to couple to a lead proximal a second cradle surface 19, wherein the lead enables electrical communication between a connection region of the array of connection regions 115 and at least one biometric sensor of the set of biometric sensors 120. As such, each connection region of the array of connection regions 115 of the mounting module 110 can be in communication (e.g., by way of one or more leads) to one or more corresponding biometric sensors 120, as described above.

Furthermore, the array of connection regions 115 can be provided in a manner analogous to that described in Sections 1.2.1 and 1.2.2, with regard to a conductive polymer used in the set of contacts 150. In particular, the array of connection regions 115 of the mounting module 110 preferably provides flexibility in maintaining robust contact between the array of connection regions 115 and the set of contacts 150 of the control module 130. Thus, any one or more of: morphological features, elastomeric portions, spring-coupled portions, and any other suitable feature of integrated with the array of connection regions 115 can provide flexible coupling between the array of connection regions 115 and the set of contacts 150. Additionally or alternatively, one or more portions of the mounting module 110 (e.g., a flexible circuit board of the mounting module 110) can be supported by a compliant material (e.g., rubber, polymer, gel, foam, etc.) in order to provide flexibility and/or a cushion at the interface between the control module 130 and the mounting module 110.

Thus, the set of layers 111 of the example function to bias the set of contacts 150 of the control module 130 into electromechanical communication with the array of connection regions 115 of the mounting module 110, to enable reception of biopotential signals from the set of biometric sensors 120 at the control module 130.

The location of mounting module 110 is preferably dependent upon the type(s) of garment(s) included in the system 100. For instance, for a garment 105 configured as a top, the mounting module 110 is preferably located at a position that does not interfere with physical activity (e.g., weight lifting activity) of the user, generate significant signal interference with one or more of the set of biometric sensors 120, or interfere with the user/signal reception in any other suitable manner. In one example, the mounting module 110 can be positioned proximal the triceps or biceps muscle of the user, when the garment 105 is worn by the user. In another example, the mounting module 110 can be centrally located between the pectoralis muscles of the user and/or the abdominal muscles of the user, when the garment 105 is worn by the user. In another variation wherein the garment 105 is configured as a bottom, the mounting module 110 can be located proximal the vastus lateralis muscle(s) of the user when the garment 105 is worn by the user. Additionally or alternatively, the system 100 can comprise multiple mounting modules no, such that the control module can be repositioned when the user is performing different types of physical activity. For example, a first mounting module positioned at an anterior portion of the garment 105 can allow the user to comfortably perform sit-ups or other exercises where the user is lying face-up, and a second mounting module positioned at a posterior portion of the garment 105 can allow the user to comfortably perform exercise where the user is lying face-down.

As noted earlier with respect to embodiments of the control module 130 including indicator LEDs, the mounting module 110 preferably allows light from the indicator LEDs to be visualized by the user wearing the garment 105. In one variation, upon insertion of the control module 130 into the mounting module 110, exposed LED indicators can be activated (e.g., by the control module 130) in order to indicate that the control module 130 has been properly seated within the mounting module 110 and is in a state to receive signals from the set of biometric sensors 120. As such, in coupling with the mounting module 110, the control module 130 can perform one or more of: detecting proper seating within the mounting module 110, determining an orientation of the control module 130 within the mounting module 110, determining, based upon the orientation of the control module, which indicator LED(s) are exposed to the user, activating the exposed indicator LED(s), not activating the unexposed indicator LED(s), and performing any other suitable function.

While the array of connection regions 115 is described in relation to the mounting module 110, the array of connection regions 115 can alternatively be integrated with the garment 105, in variations of the system 100 wherein the control module 130 is not configured to be removably coupleable to the garment 105 by way of a mounting module 110. As such, variations of the system 100 can alternatively omit a mounting module 110 and instead provide direct coupling between the set of biometric sensors 120 and the control module 130 without an intermediate mounting module 110. Variations of the system 100 can, however, be configured in any other suitable manner.

Additionally or alternatively, the mounting module 110 can comprise a first locking portion that is configured to interact with a second locking portion on the housing 140 of the control module 130, in order to facilitate maintenance of contact between the set of contacts 150 of the control module 130 and the array of connection regions 115 of the mounting module 110. In one example, the housing 140 of the control module 130 can define a notch 401 configured to reversibly couple with a latch 402 of a portion of the mounting module 110, as shown in FIG. 8C. However, the housing 140 of the control module 130 can be configured to reversibly or irreversibly lock with the mounting module 110 using any other suitable mechanism, including one or more of a snap fit mechanism, a press fit mechanism, a magnetic mechanism, and any other suitable mechanism.

1.4 System—Processing Subsystem

In some variations, the system 100 can further include a processing subsystem 170 configured to communicate with the electronics subsystem 160 and generate analyses based upon biometric signals detected by way of the set of biometric sensors. The processing subsystem 170 is preferably configured to perform at least a portion of the method 200 described in section 2 below; however, the processing subsystem 170 can alternatively be configured to perform any other suitable method. As such, the processing subsystem 170 is configured to be in communication with the electronics subsystem 160 over the network associated with the communication interface, and can further be configured to be in communication with an electronic device 180 of the user over the network. As such, analyses generated using the processing subsystem 170 can be transmitted to the electronic device 180 of the user in order to inform the user regarding his/her exercise behavior.

The processing subsystem 170 can comprise any suitable general purpose processing subsystem, which can include any one or more of: a central processing unit (CPU), a microprocessor, a digital signal processor (DSP), a microcontroller, a cloud-based computing system, a remote server, a state machine, an application-specific integrated circuit (ASIC), a programmable logic device (PLD), a field programmable gate array (FPGA), any other suitable processing device, and any suitable combination of processing devices (e.g., a combination of a DSP and a microprocessor, a combination of multiple microprocessors, etc.). For instance, in some variations, the processing subsystem 170 can be implemented in multiple modules including one or more of a DSP module of the electronics subsystem 160 having embedded algorithms, a module executing on a remote server, a module executing in a cloud-based computing system, and any other suitable module.

One or more of the elements of the electronics subsystem 160 and the processing subsystem 170 can be implemented in coordination with an electronic device 180 of the user or in proximity to the user, as the user performs physical activities. For instance, a mobile device and/or a wearable computing device (e.g., head-mounted computing device, wrist-mounted computing device, etc.) can implement indication, processing, and/or analysis provisions of the system 100, in cooperation with other elements of the system 100.

Additionally or alternatively, the electronic device 180 of the user can facilitate execution of an exercise monitoring application, in cooperation with data processing, analysis generation, and information transmission from other elements of the system 100. The exercise monitoring application can implement hardware and/or software components used for obtaining activity data from the system 100, and for performing operations on and analyses of the activity data. In one variation, the exercise monitoring application can utilize the activity data to determine one or more exercise-related metrics (e.g., total effort output, average heart rate throughout a workout, average heart rate throughout a portion of a workout, a breakdown of muscle exertion for different muscle groups, exercise progress-related metrics, etc.) representative of the user's exercise behavior, and can additionally or alternatively generate a report including the exercise-related metrics and present the report to the user within a graphical user interface (e.g., incorporating a display device, incorporating a touchscreen device). Thus, the exercise monitoring application can allow the user to monitor effectiveness of one or more exercise activities he/she performs, as well as progress in aspects of the user's performance of one or more exercise activities. In utilizing the GUI provided by the electronic device 180, the electronic device 180 can be configured to display a virtual representation of different muscle groups of the user, and/or a graphic that depicts near-real-time feedback of muscle activity of the user in association with the virtual representation of different muscle groups of the user. As such, exercise-monitoring application executing on the electronic device 180 can be used to provide near-real-time feedback to the user as the user is performing a workout regimen.

Similar to other elements of the system 100, the electronic device 180 can include a storage module configured to store activity data, performance data, and/or generated reports within a database. The storage module can be implemented at the electronic device 180 and/or on a remote computing device, and preferably facilitates documentation and provision of historical exercise information to the user. Similar to the control module 130, the electronic device 180 can further include a communication interface that allows the electronic device to communicate information over the network associated with the control module 130, or any other suitable network(s). As such, an application executing at the electronic device 180 can facilitate interaction between the user and an exercise community. In one example, the application can be configured to upload exercise-related metrics, through a network, to be shared with a community of individuals with similar fitness interests, goals, or any other suitable association with the user, and the user may be able to obtain exercise advice and/or exercise-related metrics from the community of individuals to motivate the user according to his/her goals.

In expanding upon configurations of an exercise-monitoring application being executed at the electronic device 180, the application can be configured to provide a virtual coaching environment that includes one or more of: training plans, recovery plans, information regarding competitions (e.g., training regimens configured to prepare the user for an upcoming competition), instructions for stretching, instructions for injury prevention, instructions regarding proper form for conducting an exercise, and any other suitable coaching functions. Additionally or alternatively, the application can be configured to provide alerts to the user based upon received and processed data. For instance, the application can be configured to notify the user or another entity if the user is focusing too much on a particular exercise or muscle group (e.g., by visually showing the muscle group(s) that are overemphasized and recommending other exercises to the user), or if the user is using a muscle group incorrectly during an exercise (e.g., if the user is demonstrating poor form). Additionally or alternatively, the application can provide comprehensive reports pertinent to the user's exercise behavior, including one or more of: a muscle breakdown of work performed/output for specific muscles; a breakdown of a score given for a workout, wherein the score can be tracked over time to monitor progress of the user; a classification of exercise as cardio-based or strength-based; indications of muscle atrophy, indications of rehabilitation progress; indications of fatigue; indications of potential or actual injury; and any other suitable reported factor. In one example, a report can provide a percentage of a workout associated with strength-based exercise vs. a percentage of a workout associated with cardio-based exercise. In another example, the report can additionally or alternatively provide a detailed breakdown of any exercise metric associated with one or more muscle groups, provided within a virtual display of various muscle groups. In this example, the application can be configured to accept a user input of a selection of one or more muscle groups (e.g., by selecting a portion of the virtual display of various muscle groups), and to provide relevant metrics pertaining to the muscle group(s) selected by the user.

Additionally or alternatively, the application executing at the electronic device 180 can be configured to display information directly related to muscle groups the user is monitoring, and/or to display information associated with muscle groups that the user is not actively monitoring, according to information acquired from muscle groups that the user is monitoring. As such, information from monitored muscles can be indicative of a problem elsewhere in the user's body, and monitored muscle groups can be used to provide indications or alerts pertaining to other portions of the user's body. In one example, monitored muscle groups can generate an alert that the user is positioning his bicycle seat at too high of a position, which is adversely affecting non-monitored muscle groups; in another example, monitored muscle groups can generate an alert that the user is running in a pigeon-toed manner, which is adversely affecting non-monitored muscle groups. The application(s) of the electronic device 180 can, however, be configured in any other suitable manner.

Furthermore, the system 100 can include any other suitable element(s) configured to detect and process biosignals data. Furthermore, as a person skilled in the art will recognize from the previous detailed description and from the figures and claims, modifications and changes can be made to the system 100 without departing from the scope of the system 100.

2. Method

Figure 10:
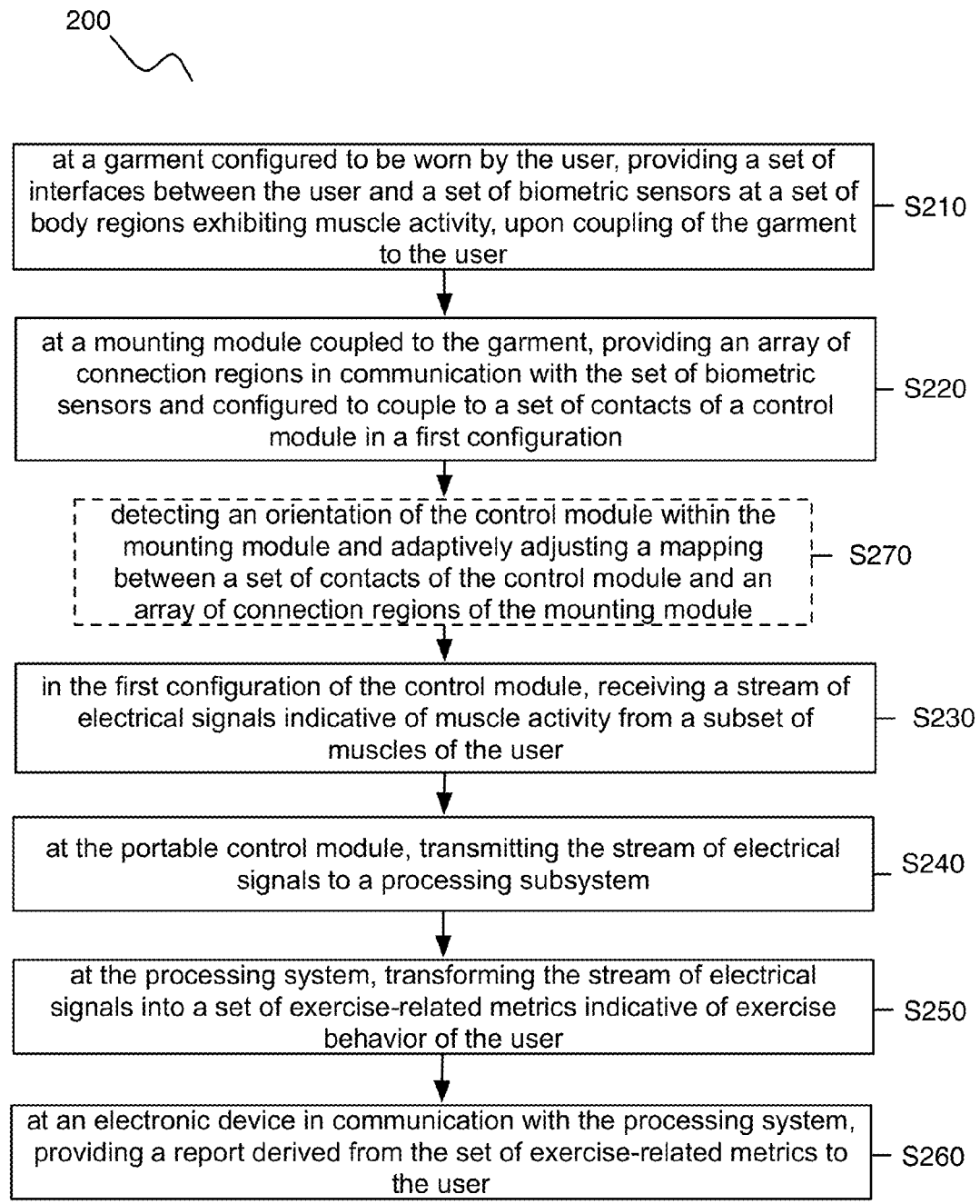
FIG. 10 depicts a flow chart of an embodiment of a method for monitoring biometric signals of a user.

As shown in FIG. 10, an embodiment of a method 200 for monitoring biometric signals of a user comprises: at a garment configured to be worn by the user, providing a set of interfaces between the user and a set of biometric sensors at a set of body regions exhibiting muscle activity, upon coupling of the garment to the user S210; at a mounting module coupled to the garment, providing an array of connection regions in communication with the set of biometric sensors and configured to couple to a set of contacts of a portable control module in a first configuration S230; at the portable control module, receiving a stream of electrical signals indicative of muscle activity from a subset of muscles of the user, in the first configuration S230; at the portable control module, transmitting the stream of electrical signals to a processing subsystem S240; at the processing subsystem, transforming the stream of electrical signals into a set of exercise-related metrics indicative of exercise behavior of the user S250; and at an electronic device in communication with the processing subsystem, providing a report derived from the set of exercise-related metrics to the user S260.

The method 200 functions to facilitate positioning of a set of biometric sensors at desired regions of a user's body, in order to detect biometric signals generated during physical activity of the user. The method 200 also functions to process detected biometric signals and to provide information derived from the processed biometric signals to the user performing a physical activity in substantially near real time, such that the user can gain insights into how to maintain or improve performance of the physical activity in a beneficial manner. In variations, the method 200 is configured to detect and process bioelectrical signals generated at a set of regions of the body of a user who is exercising (e.g., performing aerobic exercise, performing anaerobic exercise), and to present analyses in a visual manner (e.g., graphic manner, textual manner) by way of an application executing at an electronic device having a display. As such, bioelectrical signals detectable, processable, and/or analyzable according to the method 200 can include any one or more of: electromyograph (EMG) signals, electrocardiography (ECG) signals, electroencephalograph (EEG) signals, magnetoencephalograph (MEG) signals, galvanic skin response (GSR) signals, electrooculograph (EOG) signals, and any other suitable bioelectrical signal of the user. The method 200 can, however, be configured to detect, process, and/or analyze any other suitable biosignal data of the user, including one or more of: heart rate data, movement data, respiration data, location data, environmental data (e.g., temperature data, light data, etc.), and any other suitable data. The method 200 is preferably implemented at least in part at an embodiment of the system 100 described in Section 1 above; however, the method 200 can alternatively be implemented at any other suitable system for detection and processing of biometric signals from a user who is performing a physical activity.

Block S210 recites: at a garment configured to be worn by the user, providing a set of interfaces between the user and a set of biometric sensors at a set of body regions exhibiting muscle activity, upon coupling of the garment to the user. Block S210 is preferably implemented at embodiments, variations, and/or examples of the garment and the set biometric sensors described in Section 1 above; however, Block S210 can alternatively be implemented using any other suitable garment with coupled biometric sensors that are configured to detect biopotential signals indicative of muscle activity of the user. Providing the set of interfaces thus functions to provide and maintain tight coupling between sensing portions of a set of biometric sensors and desired body regions of the user as the user performs a physical activity. In providing the set of interfaces, Block S210 preferably utilizes conductive materials coupled to the garment and configured to maintain contact with the skin of the user as the user exercises; however, Block S210 can produce the set of interfaces in any other suitable manner.

In Block S210, providing the set of interfaces preferably includes generation of interfaces configured to adequately conduct one or more of: electromyography (EMG) signals, motion signals (e.g., from an accelerometer, from a gyroscope), respiration signals (e.g., respiration rate, depth of breath, thoracic variations, inspiratory flow characteristics, expiratory flow characteristics, etc.), galvanic skin response (GSR) signals, temperature-induced signals, vibration signals, bioimpedance signals, electrocardiography (ECG) signals, signals indicative of other cardiovascular parameters (e.g., pulse oximetry signals, blood pressure signals), and any other suitable type of signal. As such, the set of biometric sensors provided in Block S210 can facilitate detection of biosignals indicative of one or multiple types of biological/physiological responses to activity of a user, in providing information relevant to exercise behavior of the user.

Preferably, providing the set of interfaces in Block S210 is dependent upon the type of garment (e.g., top or bottom) provided in Block S210. Additionally, for anatomical regions having contralateral pairs, providing the set of interfaces preferably includes providing pairs of interfaces, each pair including an associated first sensor at a first body region and an associated second sensor at a second body region that is a contralateral region to the first body region. In one variation, for a garment that has a form factor of a top (e.g., shirt, tank top, etc.), the set of interfaces provided in Block S210 can include interfaces between a set of EMG electrodes and skin of the user proximal one or more of: the pectoralisis muscles, the abdominal muscles, the oblique muscles, the trapezius muscles, the rhomboid muscles, the teres major muscles, the latissimus dorsi muscles, the deltoid muscles, the biceps muscles, and the triceps muscles when the garment is worn by the user. In another variation, for a garment that has a form factor of a bottom (e.g., shorts, pants, etc.), the set of interfaces provided in Block S210 can include interfaces between a set of EMG electrodes and skin of the user proximal one or more of: the gluteus maximus muscles, the gluteus medius muscles, the vastus lateralis muscles, the gracilis muscles, the semimembranosus muscles, the semitendinosis muscles, the biceps femoris, the soleus muscles, the gastrocnemius muscles, the rectus femoris muscles, the sartorius muscles, the peroneus longus muscles, and the adductor longus muscles when the garment is worn by the user. Variations of the set of interfaces provided in Block S210 can, however, be configured in any other suitable manner.

Block S220 recites: at a mounting module coupled to the garment, providing an array of connection regions in communication with the set of biometric sensors, wherein the array of connection regions is configured to couple to a set of contacts of a control module in a first configuration. Block S220 functions to enable transmission of biopotential signals generated from the body of the user, as the user exercises, from the set of sensor interfaces to a control module. Block S220 is preferably implemented at embodiments, variations, and/or examples of the garment, the control module, the mounting module, and the set biometric sensors described in Section 1 above. As such, providing the array of connection regions preferably comprises providing electrically conductive connection regions coupled between the set of biometric sensors and the mounting module in a set configuration, as described in Section 1 above, wherein a set of contacts of the control module can be coupled to the array of connection regions in a first configuration (e.g., wherein the control module is seated within the mounting module), and uncoupled from the array of connection regions in a second configuration 102 (e.g., wherein the control module is removed from the mounting module).

In variations, as discussed in relation to the control module of Section 1 above, the array of connection regions of the mounting module can be mapped to the set of contacts of the control module regardless of the orientation of the control module, such that Block S220 includes providing a symmetric array of connection regions of the mounting module, and providing a corresponding symmetric set of contacts of the control module. Furthermore, providing the array of connection regions for the control module can further include facilitating activation of indicator LEDs of the control module, wherein activation of the indicator LEDs can be triggered upon proper coupling between the array of connection regions of the mounting module and the set of contacts of the control module. While Block S220 is preferably described in relation to the system described in Section 1 above, Block S220 can alternatively be implemented using any other suitable garment with coupled biometric sensors configured to communicate with a control module.

Block S230 recites: in the first configuration of the control module, receiving a stream of electrical signals indicative of muscle activity from a subset of muscles of the user. Block S230 functions to acquire biosignal data from the user by way of the set of biometric sensors, when the control module is coupled with the garment in the first configuration. Block S230 preferably includes receiving signals from paired sensor channels (e.g., associated with paired biometric sensors of the set of biometric sensors). As such, paired biometric sensors and contacts of the set of contacts of the control module can facilitate reception of signals that can be used to determine a signal differential (i.e., a biopotential difference) across a pair of associated sensor channels.

Receiving the stream of electrical signals in Block S230 can include conditioning the stream of electrical signals S235 at a signal conditioning module, such as the signal conditioning module described in Section 1 above, in order to generate a conditioned signal stream. In conditioning the stream of electrical signals, Block S235 can include passing the stream of electrical signals through at least one of a low pass filter, a high pass, filter, a band-pass filter, and a notch filter (i.e., a band-stop filter), in order to preprocess the datasets to remove a portion of any artifacts or interference (e.g., due to noise). In variations, the low pass filter can function to remove higher frequency noise and the high pass filter can function to remove lower frequency noise (e.g., due to waist movement/pressure artifacts). Any of the filters can further be supplemented with filters configured to remove or mitigate the frequency spectrum of any known noise components. Additionally or alternatively, Block S235 can include any one or more of: smoothing, clipping, deconvolving, detrending/offsetting, standardizing, resampling, hard-binding, predicting, windowing, and performing any other suitable data conditioning process upon any signals received in Block S230. In variations, S230 can further include storing conditioned or unconditioned signal data in memory, as describe in relation to the memory of the electronics subsystem in Section 1 above.

Block S240 recites: at the portable control module, transmitting the stream of electrical signals to a processing subsystem, which functions to transmit conditioned and/or unconditioned data derived from the stream of signals for additional processing. Block S240 is preferably implemented at an embodiment, variation, or example of the communication interface(s) described in relation to the electronics subsystem of the control module described in Section 1 above, whereby signal transmission is performed over a network associated with the control module and the processing subsystem. Transmitting the stream of electrical signals in Block S240 can be performed substantially continuously (e.g., every second, every millisecond, etc.) and/or in near-real-time, thereby facilitating near-real-time provision of comprehensive feedback to the user. Alternatively, transmitting the stream of electrical signals in Block S240 can be performed intermittently (e.g., only when the control module is coupled to the garment, at random time points, etc.) and/or in non-real-time. Furthermore, according to variations of the communication interface described in Section 1 above, transmitting the signals in Block S240 can involve wireless and/or wired transmission of data derived from the stream of electrical signals to the processing subsystem.

Block S250 recites: at the processing subsystem, transforming the stream of electrical signals into a set of exercise-related metrics indicative of exercise behavior of the user. Block S250 functions to generate an analysis derived from the stream of electrical signals received in Block S240, which can be used to provide feedback to the user regarding aspects of his/her exercise behavior. Block S250 can include determining metrics including one or more of: a metric related to effort output (e.g., total effort output as a ratio between an amount of work performed by a muscle group and a maximum amount of work that can be performed by the muscle group), a metric derived from an amount of cardio-activity performed by the user, a metric derived from an amount of strength-based activity performed by the user, a metric related to balance in utilization of all muscles of a muscle group; a metric related to a total number of muscles/ muscle groups utilized during one or more exercises, a metric related to a number of repetitions of a performed exercise, a metric related to a number of sets of a performed exercise, a metric related to a distance conquered or time duration of an exercise, a metric associated with improperness or properness of form in performing one or more exercises (e.g., as identified by signals of the signal stream indicative of muscles the user is using to perform an exercise, in relation to a desired group of muscles the user should use to perform the exercise with proper form), a metric related to target intensity level (e.g., as determined using a target intensity level desired by the user or another entity associated with the user, in relation to actual intensity level indicated by signals of the signal stream), a metric related to average heart rate throughout a workout, a metric related to average heart rate throughout a portion of a workout, a breakdown of muscle exertion for different muscle groups, exercise progress-related metrics, and any other suitable metrics. In generating any one or more of the above metrics, the processing system can be configured to utilize time information and signal feature information (e.g., amplitude, frequency, signal signatures, etc.) in determining metrics associated with individual muscles, groups of muscles, and overall assessments of activity of the user.

Block S260 recites: at an electronic device in communication with the processing subsystem, providing a report derived from the set of exercise-related metrics to the user. Block S260 preferably involves processing of the set of exercise-related metrics into a report that provides insights to the user, pertaining to the user's exercise behavior. Block S260 preferably implements an embodiment, variation, or example of the processing subsystem, electronic device, and network described in Section 1 above; however, Block S260 can additionally or alternatively be implemented using any other suitable processing and information provision elements. In providing the report(s), Block S260 preferably utilizes an exercise-monitoring application being executed at the electronic device, an example of which is shown in FIG. 11A. The report(s) can contribute to a virtual coaching environment that includes one or more of: training plans, recovery plans, information regarding competitions (e.g., training regimens configured to prepare the user for an upcoming competition), instructions for stretching, instructions for injury prevention, instructions regarding proper form for conducting an exercise, and any other suitable coaching functions derived from metrics associated with the user's muscular activity.

Additionally or alternatively, the report(s) provided in Block S260 can be used to provide alerts to the user based upon received and processed data, an example of which is shown in FIG. 11B. For instance, Block S260 can include notifying the user or another entity if the user is focusing too much on a particular exercise or muscle group (e.g., by visually showing the muscle group(s) that are overemphasized and recommending other exercises to the user), or if the user is using a muscle group incorrectly during an exercise (e.g., if the user is demonstrating poor form). Additionally or alternatively, the reports can provide synopses pertaining to one or more of: a muscle breakdown of work performed/output for specific muscles; a breakdown of a score given for a workout, wherein the score can be tracked over time to monitor progress of the user; a classification of exercise as cardio-based or strength-based; indications of muscle atrophy, indications of rehabilitation progress; indications of fatigue; indications of potential or actual injury; and any other suitable reported factor. In one example, a report can provide a percentage of a workout associated with strength-based exercise vs. a percentage of a workout associated with cardio-based exercise. In another example, the report provided in Block S260 can additionally or alternatively provide a detailed breakdown of any exercise metric associated with one or more muscle groups, provided within a virtual display of various muscle groups.

The method 200 can further include Block S270, as shown in FIG. 10, which recites: detecting an orientation of the control module within the mounting module and adaptively adjusting a mapping between a set of contacts of the control module and an array of connection regions of the mounting module. Block S270 functions to enable proper signal reception and processing from a symmetric control module that can be coupled to the garment in multiple orientations. Block S270 can implement contact configuration(s) of the set of contacts of the control module and any other suitable data (e.g., accelerometer data, gyroscope data) in order to detect the orientation of the control module relative to the garment. Once the orientation of the control module is detected, Block S270 can include adapting signal reception and processing functions accordingly. As such, Block S270 can allow the control module to operate properly regardless of how the control module is coupled with the garment, in receiving and processing signals from the set of biometric sensors. For example, using the contact configuration shown in FIG. 6, signals X and Y can be received by way of contacts 1A and 1B in a first orientation of the control module, but if the control module is positioned "upside-down" in a second orientation, firmware implementing Block S270 can adapt signal reception and processing of the control module to receive signals X and Y by way of contacts 14B and 14A, respectively. As such, in the example, Block S270 can facilitate dynamic modification of the contact mapping in order to property attribute signals X and Y to the correct muscle group or set of biometric sensors.

Additionally or alternatively, Block S270 can include post-processing of signals based upon supplementary data that can allow signatures associated with one or muscle groups or types of activity to be identified. For instance, if accelerometer data indicates motion behavior associated with a first muscle group, but EMG signal data indicates muscle activity not associated with the first muscle group, Block S270 can involve reconfiguring a mapping between the set of contacts of the control module and the set of biometric sensors, post-reception of the signal stream from the set of biometric sensors, and generating metrics and reports according to the reconfigured mapping. Any other signatures derived from one or more of: gyroscope data, accelerometer data, GPS data, temperature data, location data, heart rate data, and any other suitable data can be used to identify the most probable muscle groups being used in an activity, and adjusting a mapping between the set of contacts of the control module accordingly. As such, identification of the configuration of the control module relative to the garment can be facilitated based upon cross-correlation between different types of data (e.g., accelerometer data, EMG sensor data), detection of identification contact configurations, and/or in any other suitable manner.

The method 200 can further include any one or more of: detecting misalignment of the control module, providing an indication of misalignment of the control module (e.g., using indicator LEDs), receiving a user input and providing a customized report based upon the user input (e.g., allowing the user to select a portion of a virtual display of various muscle groups and providing a report based upon the selection), allowing the user to receive information and feedback (e.g., training information, motivational feedback) from a community of associated users, and any other suitable steps or blocks that promote proper exercise behavior of the user.

Variations of the system 100 and method 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for providing an electrical signal conduction pathway in a waterproof manner, the system including:
   a first housing portion including an array of openings;
   an electronics connection substrate, coupled to the first housing portion and including a set of electrical contact pads; and
   set of contacts, each contact in the set of contacts composed of a conductive polymer and having 1) a first region that seals, in a watertight manner, an opening of the array of openings of the first housing portion at an exterior surface of the first housing portion, 2) an intermediate region that passes into the opening of the array of openings, and 3) a second region coupled to an electrical contact pad of the set of electrical contact pads,
   wherein each electrical contact pad in the set of electrical contact pads includes a port through which the second region of at least one contact of the set of contacts is coupled, and
   wherein each contact in the set of contacts is configured to conduct an electrical signal to at least one electrical contact pad of the electronics connection substrate for signal transmission to an electronics subsystem.

2. The system of claim 1, wherein the port of each electrical contact pad passes entirely through a thickness of the electronics connection substrate.

3. The system of claim 1, wherein the second region of each contact passes through a corresponding port of the set of electrical contact pads, and is molded to a second surface of the electronics connection substrate.

4. The system of claim 1, wherein each contact of the set of contacts is composed of an electrically conductive polymer.

5. The system of claim 1, wherein the electronics connection substrate comprises a flexible printed circuit board that complies with an internal surface of the first housing portion, and wherein the system further includes a linking interface that couples each of the set of electrical contact pads to the electronics subsystem for signal processing and transmission.

6. The system of claim 1, wherein the set of electrical contact pads of the electronics connection substrate is paired with the array of openings of the first housing portion in a one-to-one manner.

7. The system of claim 1, wherein each contact of the set of contacts is physically isolated from adjacent contacts of the set of contacts, and wherein the first housing portion is composed of a non-electrically conductive material.

8. The system of claim 1, further comprising a second housing portion coupled to the first housing portion, with a water tight seal at an interface between the first housing portion and the second housing portion.

9. The system of claim 8, wherein the first housing portion and the second housing portion enclose a) the intermediate regions and the second regions of the set of contacts, b) the electronics connection substrate, and 3) the electronics subsystem.

10. A system for providing an electrical signal conduction pathway in a waterproof manner, the system including:
    A housing including an array of openings;
    A set of electrical contact pads included within the housing; and
    A set of contacts, each contact composed of a conductive polymer and protruding into a corresponding opening in the array of openings and coupling to a corresponding electrical contact pad of the set of electrical contact pads such that electrical signals are conducted from the corresponding electrical contact pad to an electronics subsystem via the corresponding opening by the contact, wherein the conductive polymer forms a watertight seal with the corresponding opening.

11. The system of claim 10, wherein each contact of the set of contacts comprises an electrically conductive polymer.

12. The system of claim 10, further comprising a flexible printed circuit board that complies with an internal surface of the housing, and wherein the system further includes a linking interface that couples each of the set of electrical contact pads to the flexible printed circuit board.

13. The system of claim 10, wherein each of the set of electrical contact pads is paired to a different opening of the array of openings.

14. The system of claim 10, wherein each contact of the set of contacts is physically isolated from adjacent contacts of the set of contacts, and wherein the housing comprises a non-electrically conductive material.

15. The system of claim 10, wherein the housing forms a water tight seal around each opening of the set of openings.

16. The system of claim 10, wherein each electrical contact pad in the set of electrical contact pads includes a port through which the conductive polymer of at least one contact of the set of contacts is coupled.

17. The system of claim 16, wherein the port of each electrical contact pad passes entirely through an opening of the array of openings.

18. The system of claim 16, wherein the each electrical contact pad is molded to an electronics connection substrate.

* * * * *